US012797218B2

(12) United States Patent
Radl et al.

(10) Patent No.: US 12,797,218 B2
(45) Date of Patent: Nov. 17, 2026

(54) ILLUMINATED INSTRUMENTS FOR BARIATRIC SURGERY AND METHODS OF BARIATRIC SURGERY

(71) Applicant: Boehringer Technologies, LP, Phoenixville, PA (US)

(72) Inventors: Christopher L. Radl, Malvern, PA (US); Trevor G. Smith, West Chester, PA (US); Ondrej Nikel, King of Prussia, PA (US)

(73) Assignee: Boehringer Technologies, LLC, Phoenixville, PA (US)

( * ) Notice: Subject to any disclaimer, the term of this patent is extended or adjusted under 35 U.S.C. 154(b) by 267 days.

(21) Appl. No.: 18/605,334

(22) Filed: Mar. 14, 2024

(65) Prior Publication Data

US 2024/0216160 A1 Jul. 4, 2024

Related U.S. Application Data

(63) Continuation-in-part of application No. 17/136,407, filed on Dec. 29, 2020, now Pat. No. 12,303,415,
(Continued)

(51) Int. Cl.
*A61B 17/00* (2006.01)
*A61B 17/072* (2006.01)
(Continued)

(52) U.S. Cl.
CPC ...... *A61F 5/0089* (2013.01); *A61B 17/07207* (2013.01); *A61B 2017/00818* (2013.01);
(Continued)

(58) Field of Classification Search
CPC ........ A61F 5/0089; A61B 2017/00818; A61M 25/007
See application file for complete search history.

(56) References Cited

U.S. PATENT DOCUMENTS

| | | | |
|---|---|---|---|
| 3,565,076 | A | 2/1971 | Kadan |
| 3,888,249 | A | 6/1975 | Spencer |

(Continued)

FOREIGN PATENT DOCUMENTS

| | | | |
|---|---|---|---|
| KR | 101263937 | B1 | 5/2013 |
| WO | 2010/115473 | A1 | 10/2010 |

(Continued)

OTHER PUBLICATIONS

Ethicon Endo-Surgery, Gastric Calibration Tube—Instructions for Use, 2012, pp. 1-8.

(Continued)

*Primary Examiner* — Daniel L Cerioni
(74) *Attorney, Agent, or Firm* — Caesar Rivise, PC

(57) ABSTRACT

Systems and methods for effecting bariatric procedures are disclosed. Each system includes an instrument, a control valve and, optionally, a suction controller. The instrument is in the form of an elongated, flexible sizing tube having a distal end portion including plural apertures through which suction is applied for anchoring the sizing tube in the patient's stomach and for forming a visually perceptible delineation line on the exterior of the patient's stomach along which a portion of the stomach may be resected, sealed and tested. The elongated flexible sizing tube includes a source of illumination to produce near infrared light to facilitate the location of the sizing tube within the patient's stomach and to provide visual information about location of certain relevant internal anatomical features.

19 Claims, 13 Drawing Sheets

Related U.S. Application Data which is a continuation of application No. 15/730,332, filed on Oct. 11, 2017, now Pat. No. 10,888,446, which is a continuation of application No. 14/073,464, filed on Nov. 6, 2013, now Pat. No. 9,808,368.

(60) Provisional application No. 61/837,908, filed on Jun. 21, 2013, provisional application No. 61/777,432, filed on Mar. 12, 2013, provisional application No. 61/731,200, filed on Nov. 29, 2012.

(51) Int. Cl.
*A61F 5/00* (2006.01)
*A61B 17/30* (2006.01)
*A61B 17/32* (2006.01)
*A61J 15/00* (2006.01)
*A61M 25/00* (2006.01)

(52) U.S. Cl.
CPC .................. *A61B 2017/306* (2013.01); *A61B 2017/320052* (2013.01); *A61J 15/0003* (2013.01); *A61M 25/007* (2013.01)

(56) References Cited

U.S. PATENT DOCUMENTS 5,382,231 A 1/1995 Shlain
5,405,316 A 4/1995 Magram
5,879,306 A * 3/1999 Fontenot .............. A61B 1/3132 600/476
5,992,239 A 11/1999 Boehringer et al.
6,024,120 A 2/2000 Yam et al.
7,438,705 B2 10/2008 Karpowicz et al.
7,686,785 B2 3/2010 Boehringer et al.
7,857,806 B2 12/2010 Karpowicz et al.
7,896,894 B2 3/2011 Ortiz et al.
8,211,128 B1 7/2012 Facundus et al.
8,382,775 B1 2/2013 Bender
8,663,149 B2 3/2014 Gagner et al.
9,375,137 B2 6/2016 Sherwinter
9,999,533 B2 6/2018 Radl et al.
10,182,933 B2 1/2019 Rokde et al.
10,646,625 B2 5/2020 Radl et al.
10,888,446 B2 1/2021 Radl et al.
10,932,937 B2 3/2021 Radl et al.
11,389,266 B2 7/2022 Szoka
11,389,318 B2 7/2022 Radl et al.
11,543,350 B2 1/2023 Thorwarth
2002/0183768 A1 12/2002 Deem et al.
2003/0120265 A1 6/2003 Deem et al.
2004/0133147 A1 7/2004 Woo
2004/0133226 A1 7/2004 Buckman et al.
2005/0113798 A1 5/2005 Slater et al.
2005/0251158 A1 11/2005 Saadat et al.
2005/0261663 A1 11/2005 Patterson et al.
2006/0025727 A1 2/2006 Boehringer et al.
2006/0106288 A1 5/2006 Roth et al.
2006/0200191 A1 9/2006 Zadno-Azizi
2007/0032702 A1 2/2007 Ortiz
2007/0032800 A1 2/2007 Ortiz et al.
2007/0175488 A1 8/2007 Cox et al.
2008/0015504 A1 1/2008 Boehringer et al.
2008/0249404 A1 10/2008 Mikkaichi et al.
2008/0275473 A1 11/2008 Filipi et al.
2009/0012544 A1 1/2009 Thompson et al.
2009/0126744 A1 5/2009 Bessler
2009/0275937 A1 11/2009 Stokes et al.
2009/0275960 A1 11/2009 Provenza et al.
2010/0191264 A1 7/2010 Kassab et al.
2011/0178454 A1 7/2011 Gagner et al.
2011/0184338 A1 7/2011 McKay
2011/0288576 A1 11/2011 Hoffman
2011/0295286 A1 12/2011 Harris et al.
2012/0004677 A1 1/2012 Balbierz
2012/0016393 A1 1/2012 Murray et al.
2012/0123463 A1 5/2012 Jacobs
2012/0238972 A1 9/2012 Karpowicz et al.
2012/0277525 A1 11/2012 O'Dea
2013/0066297 A1 3/2013 Shtul et al.
2013/0085438 A1 4/2013 MacMeans et al.
2013/0131440 A1 5/2013 Gabriel
2013/0153626 A1* 6/2013 Felder .................. A61B 17/068 227/175.1
2013/0165774 A1 6/2013 Nocca
2013/0178698 A1 7/2013 Bender et al.
2013/0178877 A1 7/2013 Bender et al.
2014/0018722 A1 1/2014 Scott et al.
2014/0039278 A1 2/2014 Birk
2014/0073858 A1 3/2014 Sherwinter
2014/0081176 A1 3/2014 Hassan
2014/0107698 A1 4/2014 Inge
2014/0114121 A1 4/2014 Trivedi
2014/0148731 A1 5/2014 Radl
2014/0155918 A1 6/2014 Gagner et al.
2014/0276991 A1 9/2014 Schauer
2015/0080647 A1 3/2015 Wetter
2015/0209239 A1 7/2015 Salvino
2016/0256170 A1 9/2016 Busold et al.
2018/0125690 A1 5/2018 Brister
2019/0083732 A1 3/2019 Vadivelu
2019/0117114 A1 4/2019 Marczyk et al.
2019/0144594 A1 5/2019 Maegawa et al.
2020/0305999 A1 10/2020 Szoka
2020/0347243 A1 11/2020 Klymchenko et al.
2021/0113358 A1 4/2021 Radl et al.
2022/0151724 A1* 5/2022 Szoka .................... A61B 90/30
2022/0354681 A1 11/2022 Radl et al.

FOREIGN PATENT DOCUMENTS

WO 2011/161148 A1 12/2011
WO 2012/138737 A1 10/2012
WO 2012/141679 A1 10/2012
WO 2015095333 A1 6/2015
WO 2017011085 A1 1/2017

OTHER PUBLICATIONS

Cook Surgical Products, Gastric Sizing Balloon Catheter product brochure, C-GSB905, 2005, pp. 1-4.
Boehringer Laboratories, Inc. "7700 Series Suction Regulator Technical Manual and Operating and Maintenance Instructions." (2004):1-14.
International Search Report for PCT/US2013/070073 dated Feb. 11, 2014.
International Search Report and Written Opinion for PCT/US2022/026748 dated Aug. 17, 2022.

* cited by examiner

Fig. 9
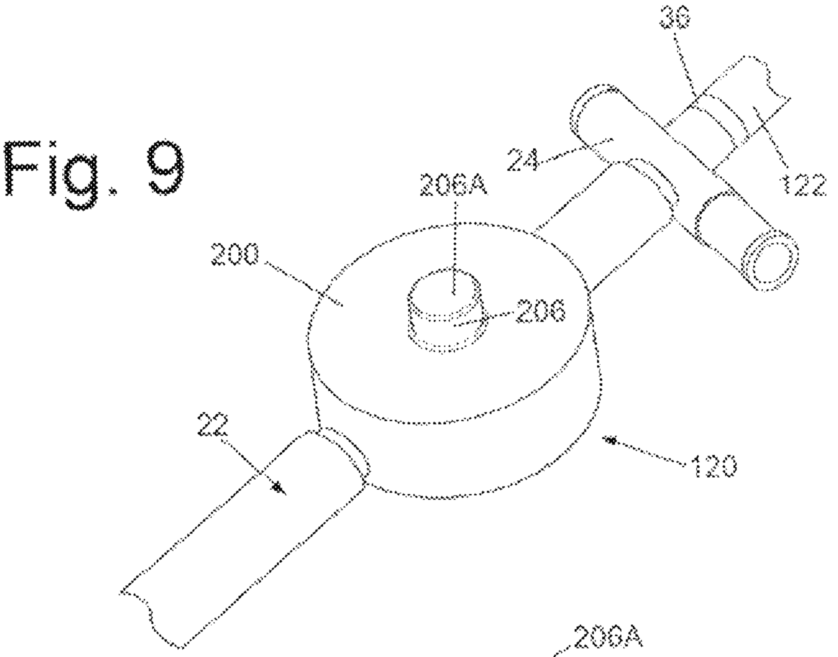
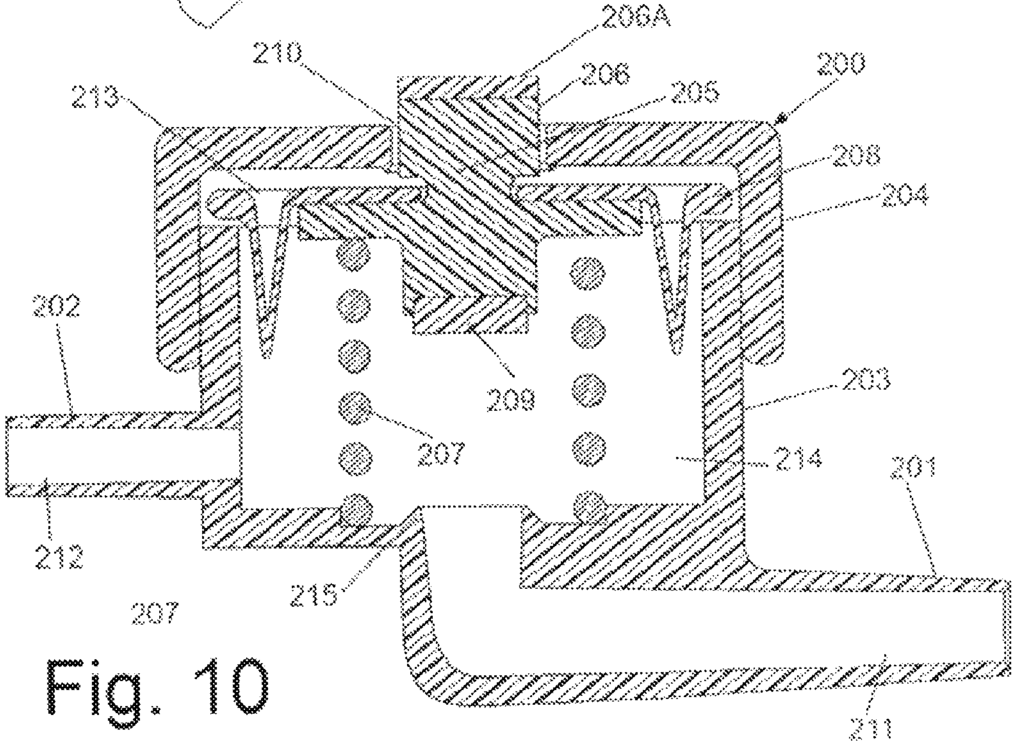
Fig. 10

Fig. 37
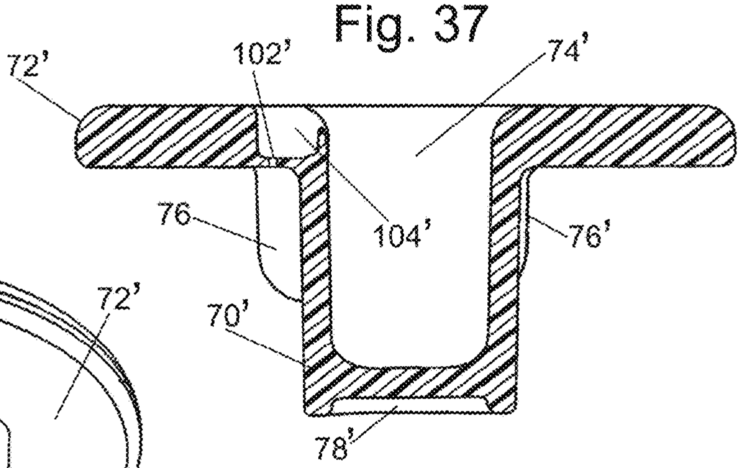
Fig. 36
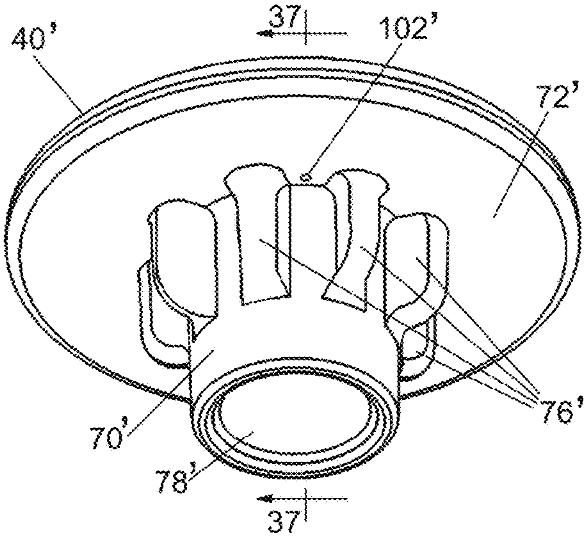
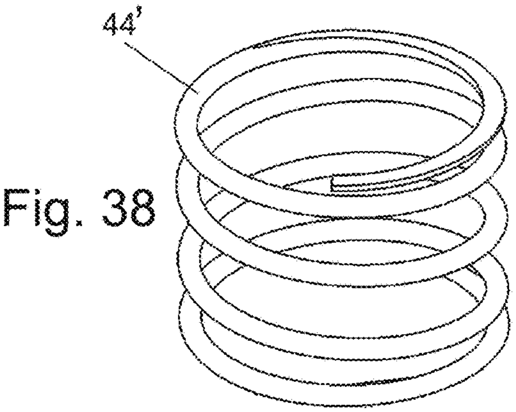
Fig. 38
Fig. 39
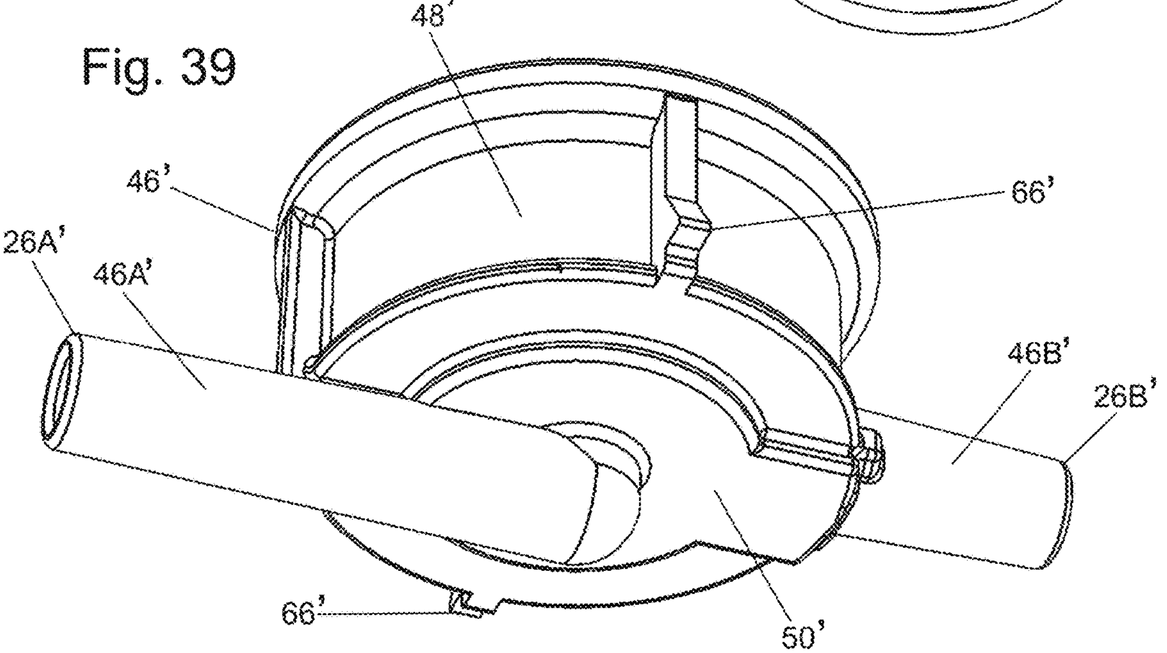

Fig. 42

ViSiGi® LUX

Calibration System
Single Patient Use

System Components

*Tubing* - The tubing is approximately 104 cm long. Model 5340 has a tube diameter of 40 French. Model 5336 has a tube diameter of 36 French. Model 5332 has a tube diameter of 32 French. (3 French = 1 mm diameter)

*Holes* - The tubes include apertures that extend to a distance of approximately 13 cm from the distal end.

*Slide Valve* - The valve is a vented 2-position valve that includes a tubing connector for connection to standard hospital suction tubing.

*Suction Regulator* - The integral suction regulator delivers regulated suction.

*Visible/Near Infrared (NIR) Lighting System* - Visible/NIR lights within the distal tip of the device are activated by removing the battery insulator pull tab. Once activated, lights will remain on for the duration of the procedure.

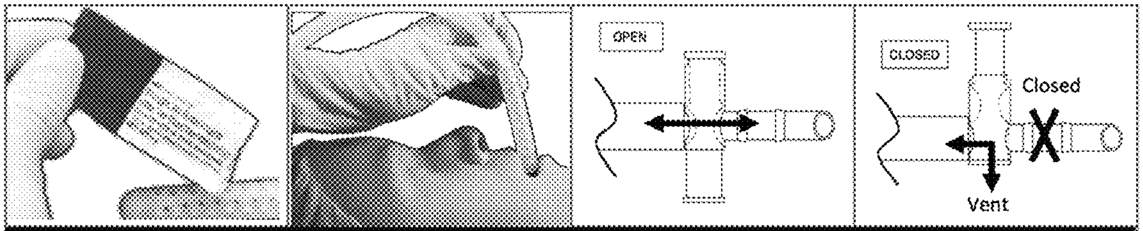

| Step 1 | Step 2 | Step 3 | Step 4 |
|---|---|---|---|
| Remove ViSiGi LUX from the clear packaging, and remove the battery insulator pull tab. Red light at the distal end of the tube indicates the device is energized. Ensure the valve is set to OPEN, and apply surgical lubricant generously onto the tip of ViSiGi LUX before inserting into patient. If using with a laparoscopic or robotic camera with NIR mode, select the appropriate camera mode to enable NIR-assisted visualization of the device. | Advance ViSiGi LUX under direct visualization by surgeon's direction, or insert the same way as an OG tube. STOP once gastric contents are visible. There are length markings at 30, 40, and 50 cm. Do not pass the third marking (50 cm) without laparoscopic visualization. | For sizing, position ViSiGi LUX within the stomach as desired and connect ViSiGi LUX to suction.<br><br>To remove fluid, enable irrigation, or to apply suction, place the slide valve in the OPEN position. | When moving or removing ViSiGi LUX, stop the suction, and vent ViSiGi LUX, by placing the slide valve in the CLOSED position. |

NOTE: If exposing the apertured portion of ViSiGi LUX directly to the peritoneal space, suction should not be applied.
NOTE: If using suction, place the slide valve in the CLOSED position prior to removing the ViSiGi LUX.
NOTE: The distal end of the ViSiGi LUX adheres to the lumen of the stomach when suction is applied. Do not pull on the device when suction is applied.
NOTE: The integral suction regulator limits suction levels to approximately 125 mm Hg. If it is desired to limit suction to lower levels, attach to a standard hospital wall suction regulator and adjust suction level accordingly.
NOTE: When using the ViSiGi LUX in the Roux-en-Y or similar procedure, prior to stapling, such as when creating the pouch, make sure that the exact location of the ViSiGi LUX is known and that it is not in the path of the stapler. One way to ensure that it is not in the path of the stapler is to withdraw the tip of the ViSiGi LUX into the esophagus.

ILLUMINATED INSTRUMENTS FOR BARIATRIC SURGERY AND METHODS OF BARIATRIC SURGERY

CROSS REFERENCE TO RELATED APPLICATIONS

This application is a Continuation-In-Part of U.S. patent application Ser. No. 17/136,407, filed on Dec. 29, 2020, entitled Systems And Methods For Performing Bariatric Surgery, which in turn is a continuation of application Ser. No. 15/730,332, filed on Oct. 11, 2017, entitled Systems And Methods For Performing Bariatric Surgery, now U.S. Pat. No. 10,888,446, which in turn is a continuation of application Ser. No. 14/073,464, filed on Nov. 6, 2013, entitled Methods For Performing Bariatric Surgery Using Gastric Sizing Systems And Instruments, now U.S. Pat. No. 9,808,368, which in turn claims priority from provisional applications: Ser. No. 61/837,908, filed on Jun. 21, 2013, entitled Gastric Sizing Instruments With Anti-Blocking Feature And Methods Of Use In Bariatric Surgery; Ser. No. 61/777,432, filed on Mar. 12, 2013, entitled Gastric Sizing Instrument And Method Of Use In Bariatric Surgery; and Ser. No. 61/731,200, filed on Nov. 29, 2012, entitled Gastric Sizing Device And Method Of Use In Bariatric Surgery, all of which applications are assigned to the same assignee as the subject invention and whose disclosures are specifically incorporated by reference herein.

FIELD OF THE INVENTION

This invention relates generally to systems and medical instruments arranged for introduction into the stomach of a patient and more particularly to systems including gastric sizing instruments for effecting bariatric metabolic surgeries, such as a Sleeve Gastrectomy.

BACKGROUND OF THE INVENTION

As is known, bariatric surgery (frequently referred to as weight-loss surgery) includes a variety of procedures performed on people who are morbidly obese. One commonly performed procedure is referred to as a sleeve gastrectomy and entails reducing the size of the stomach through removal of a portion of it. In particular, a large portion of the stomach following the stomach's lesser curve is resected, typically laparoscopically, and the open edges of the remaining portion of the patient's stomach are then attached, e.g., stapled, together to form a tube or "sleeve", leaving the patient with a stomach which is substantially smaller, e.g., about 25% of its original size.

Heretofore, sleeve gastrectomies have been accomplished by introducing a Bougie (esophageal dilator) of a specific size into the stomach via the esophagus so that it is disposed along the lesser curvature of the stomach. When in place, it provides a guide where the stomach is to be resected. The resection is typically accomplished via the use of a cutting stapler. In U.S. Pat. No. 9,999,533 (Radl et al.); U.S. Pat. No. 10,646,625 (Radl et al.); and U.S. Pat. No. 10,932,937 (Radl et al.) all of which are assigned to the same assignee as the subject application, and whose disclosures are specifically incorporated by reference herein, there are disclosed systems and methods for effecting bariatric surgery using sizing tubes which overcome various disadvantages of the prior art. In particular, the systems and methods of those patents entail an instrument, a control valve and, optionally, a suction controller. The instrument is in the form of an elongated, flexible member (referred to as a sizing tube) having a distal end portion arranged for anchoring the instrument in the patient's stomach and for enabling fluids to be removed from the patient's stomach with a plurality of apertures extending about the periphery of the sizing tube and located within a distal section of the sizing tube. Suction is applied to the patient's stomach via those apertures from a source of controlled suction coupled to a proximal portion of the sizing tube to drain gastric fluids and to bring adjacent portions of the patient's stomach into engagement with the instrument to provide a visually perceptible delineation line along which a portion of the stomach facing the greater curvature, so that a portion of the stomach may be resected, sealed and tested along that visually perceptible delineation line.

While those devices of those aforementioned patents eminently are suitable for their intended purposes, there may be instances where it is desirable to more clearly see the position of the gastric sizing tube within the stomach by the illumination thereof.

In U.S. patent application Ser. No. 17/730,434, filed on Apr. 27, 2022, entitled Gastric Sizing Systems Including Illuminating Devices And Methods Of Bariatric Surgery Using The Same, which is assigned to the same assignee as the subject application, and whose disclosure is incorporated by reference herein, there is disclosed and claimed an illuminated instrument and methods for performing bariatric surgery.

While the Bougie tube disclosed in the forgoing application and other instruments in the prior art for performing bariatric surgery may be generally suitable for its intended purpose, they still leave much to be desired from the standpoints of integrating all of the procedures necessary for a sleeve gastrectomy into one device and for providing a good visual indication of the line along which the stomach is to be resected to enable such action to be readily accomplished and to provide an instrument which is resistant to becoming stuck in the stomach.

Thus, a need exists for systems and instruments which address those needs and which can be used to perform bariatric surgery and other GI surgical procedures safely and expeditiously. The subject invention does that.

SUMMARY OF THE INVENTION

One aspect of this invention is a system for sizing a patient's stomach for a bariatric procedure. The stomach has a wall, a greater curvature and a lesser curvature. The patient also has an esophagus. The system basically comprises an instrument and a suction controller. The instrument is coupled to the suction controller. The instrument is non-expandable and comprises a sizing tube formed as an elongated unitary member of a flexible non-expandable material has a predetermined outside diameter configured for introduction through the esophagus into the patient's stomach so that a portion of the sizing tube is disposed along the lesser curvature of the patient's stomach. The sizing tube has a longitudinal axis and a circular cross-section having a circular outer surface, whereupon when the sizing tube is disposed along the lesser curvature of the patient's stomach the entire circular outer surface of the sizing tube is exposed for engagement by portions of the patient's stomach. The sizing tube has a distal end portion, a proximal end portion, a hollow interior defining a passageway, and a plurality of apertures disposed about the circular outer surface at the distal end portion. The plurality of apertures is directed in a plurality of different radial directions extending at an angle greater than zero degrees from each other measured about the longitudinal axis and is in fluid communication with the passageway. Plural ones of the apertures extend along a portion of the lesser curvature of the patient's stomach when the sizing tube is located within the patient's stomach. The suction controller is configured for producing controlled suction from a source of suction and providing the controlled suction to the passageway, whereupon controlled suction is applied to the passageway and through the apertures to pull the lesser curvature of the patient's stomach into engagement with a portion of the circular outer surface of the sizing tube and contemporaneously therewith to pull other portions of the patient's stomach adjacent to the sizing tube towards portions of the circular outer surface of the sizing tube not facing the lesser curvature of the patient's stomach and without any portion of the instrument being interposed therebetween to anchor the sizing tube in place. The controlled suction as applied by the apertures producing a suction-created visually perceptible delineation line on the exterior of the patient's stomach along a portion of the circular outer surface of the sizing tube facing the greater curvature of the patient's stomach and with the controlled suction as applied by the apertures serving as the sole means anchoring the sizing tube in place.

In accordance with one preferred aspect of the system of this invention, the instrument additionally comprises an electrical subsystem. The electrical subsystem comprises an elongated source of illumination located within the sizing tube and extending along a portion of the longitudinal axis at the distal end portion. The elongated source of illumination is configured for producing near infrared light into the patient's stomach, whereupon the position of the sizing tube within the patient's stomach can be readily visualized laparoscopically from outside the wall of patient's stomach by transillumination of the near infrared light passing through the wall of the patient's stomach.

In accordance with another preferred aspect of the system of this invention, the near infrared light is in the range of approximately 780 nm to 880 nm.

In accordance with another preferred aspect of the system of this invention, the near infrared light is preferably approximately 850 nanometers.

In accordance with another preferred aspect of the system of this invention, the elongated source of illumination comprises a flexible circuit including plural spaced-apart near infrared light emitting diodes.

In accordance with another preferred aspect of the system of this invention, the electrical subsystem additionally comprises at least one light emitting diode for producing light at a visible frequency to provide an indication of the operation of the source of illumination.

In accordance with another preferred aspect of the system of this invention, the electrical subsystem additionally comprises an electrical battery connected to the elongated source of illumination.

In accordance with another preferred aspect of the system of this invention, the sizing tube is configured to permit flexing thereof perpendicular to the longitudinal axis while preventing longitudinal collapse thereof due to perpendicular flexion.

In accordance with another preferred aspect of the system of this invention, the instrument additionally comprises a spring located in the distal end portion of the sizing tube. The spring is configured to permit flexing of the sizing tube perpendicular to the longitudinal axis while preventing longitudinal collapse of the sizing tube due to perpendicular flexion.

In accordance with another preferred aspect of the system of this invention, the sizing tube includes at least one one-way valve. The at least one one-way valve is automatically closed when controlled suction is applied to the passageway. The at least one one-way valve is openable to enable a fluid to be passed therethrough from the interior of the sizing tube into the stomach of the patient to prevent the sizing tube from becoming stuck in the patient's stomach.

In accordance with another preferred aspect of the system of this invention, the at least one one-way valve comprises a slit in the sidewall.

In accordance with another preferred aspect of the system of this invention, the suction controller is configured to apply controlled suction to the passageway of the sizing tube to result in a force in a range of 0.05 to 200 pounds anchoring the sizing tube in position within the patient's stomach.

In accordance with another preferred aspect of the system of this invention, the sizing tube is configured to apply a suction force per unit length within the patient's stomach at the location of the apertures when the controlled suction is applied to the passageway, whereupon the suction force applied per unit length is in a range of 0.02 to 21 pounds per inch.

Another aspect of this invention is a method of sizing a patient's stomach for a bariatric procedure. The method comprises providing an instrument comprising a non-expandable sizing tube formed as a unitary elongated member of a flexible non-expandable material having a predetermined outside diameter, a longitudinal axis and a circular cross-section having a circular outer surface that is entirely continuous along an entire length of the sizing tube. The sizing tube has a hollow interior defining a passageway, a distal end portion and a proximal end portion. The distal end portion terminates in a free end tip. The distal end portion has a predetermined outside diameter and a plurality of apertures disposed about the entirely continuous circular outer surface of the distal end portion. The plurality of apertures is directed in a plurality of different radial directions from the longitudinal axis and is in fluid communication with the passageway. The sizing tube is introduced into the stomach of the patient through the patient's esophagus so that a portion of the sizing tube is disposed along the lesser curvature of the patient's stomach, whereupon the entirely continuous circular outer surface of the sizing tube is exposed for engagement by portions of the patient's stomach. The passageway of the sizing tube is connected to a source of controlled suction whereupon controlled suction is applied to the interior of the patient's stomach via the plurality of apertures to pull the lesser curvature of the patient's stomach into engagement with a portion of the sizing tube without any portion of the instrument interposed between the entirely continuous circular outer surface of the sizing tube and the interior of the patient's stomach to produce a suction-created visually perceptible delineation line on the exterior of the patient's stomach along a portion of the entirely continuous circular outer surface of the sizing tube facing the greater curvature of the patient's stomach. The patient's stomach is laparoscopically sealed from the outside of the patient's stomach along a seal line that is adjacent to the visually perceptible delineation line.

In accordance with one preferred aspect of the method of this invention, the instrument additionally comprises an electrical subsystem comprising an elongated source of illumination located within the sizing tube and extending along a portion of the longitudinal axis at the distal end portion. The elongated source of illumination is configured for producing near infrared light. The elongated source of illumination is operated to introduce near infrared light into the patient's stomach or other communicating anatomical structures through the sizing tube when the sizing tube is disposed along the lesser curvature of the patient's stomach, whereupon the position of the sizing tube within the patient's stomach can be readily visualized laparoscopically from outside the wall of patient's stomach by transillumination of the near infrared light passing through the wall of the patient's stomach or other communicating anatomical structures.

In accordance with another preferred aspect of the method of this invention, the near infrared light is in the range of approximately 780 nm to approximately 880 nm.

In accordance with another preferred aspect of the method of this invention, the near infrared light is preferably approximately 850 nanometers.

In accordance with another preferred aspect of the method of this invention when the controlled suction is applied to the hollow interior of the passageway it results in a force in the range of 0.1 to 200 pounds holding the sizing tube in position.

In accordance with another preferred aspect of the method of this invention, the level of controlled suction to be applied is in the range of 25-200 mm Hg.

In accordance with another preferred aspect of the method of this invention, the controlled suction applied to the interior of the patient's stomach results in a force in a range of 0.05 to 200 pounds anchoring the sizing tube in position within the patient's stomach.

DESCRIPTION OF THE DRAWING

FIG. 9 is an isometric view of a system constructed in accordance with another aspect of this invention, wherein the system includes a suction controller (also referred to herein as a suction regulator) including an indicator constructed in accordance with one aspect of this invention for connection to a sizing device constructed in accordance with this invention;

FIG. 9A is an isometric view of another system constructed in accordance with this invention, wherein the system includes an alternative preferred suction controller or regulator;

FIG. 10 is an enlarged vertical sectional view of the suction controller/indicator shown in FIG. 9;

FIG. 10A is an enlarged vertical sectional view of the suction controller shown in FIG. 9A;

FIG. 36 is a more enlarged isometric view of the piston shown in FIG. 35;

FIG. 37 is an enlarged sectional view taken along line 37-37 of FIG. 36;

FIG. 38 is an isometric view of another of the components, i.e., a spring, of the suction regulator shown in FIG. 31;

FIG. 39 is an enlarged isometric view of another of the components, i.e., a housing, of the suction regulator shown in FIG. 31;

FIG. 42 is a reproduction of a portion of Instructions For Use of a commercial instrument, identified under the trademark VISIGI® LUX, which is constructed in accordance with the embodiment of the invention shown in FIG. 14.

DETAILED DESCRIPTION OF THE PREFERRED EMBODIMENT

Figure 1:
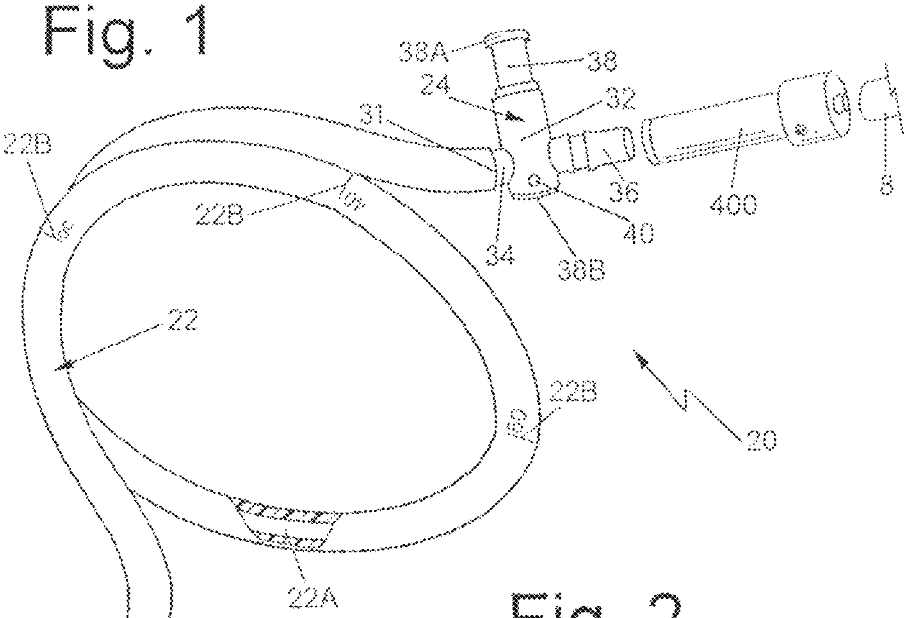
FIG. 1 is an isometric view of a portion of a system constructed in accordance with one exemplary preferred embodiment of this invention including a sizing instrument or device, e.g., a sizing tube, shown partially in section, for performing a bariatric procedure, e.g., a sleeve gastrectomy, on a patient, with the valve of the device shown in its closed or "off" position.
Figure 1:
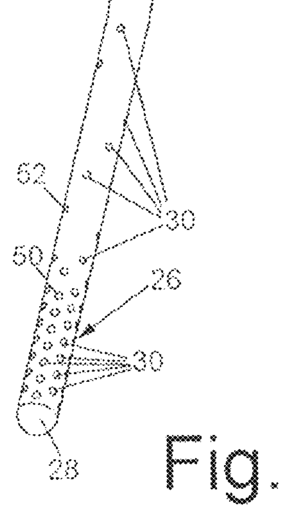
Figure 11:
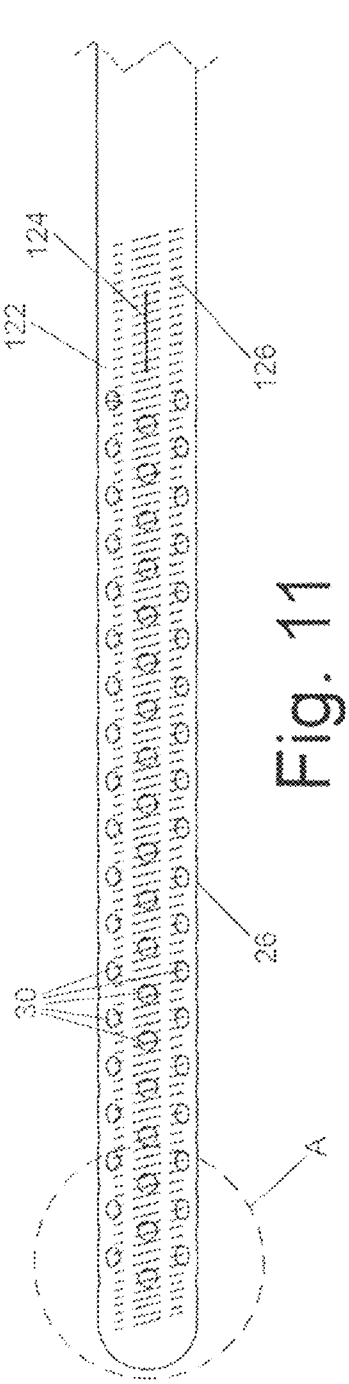
FIG. 11 is an enlarged elevation view of the distal end of an alternative preferred embodiment of a sizing device constructed in accordance with this invention.

Referring now to the various figures of the drawing wherein like reference characters refer to like parts, there is shown in FIG. 1 one exemplary embodiment of a system 20 constructed in accordance with one exemplary preferred embodiment of this invention including a sizing device or instrument for performing a bariatric procedure on a patient. FIG. 11 shows an alternative sizing tube of another system of this invention. All of the systems of this invention are particularly suitable for use in bariatric metabolic surgeries, such as a sleeve gastrectomy. However, the systems and instruments of the subject invention are not limited to such usage. Thus, the systems and instruments of the subject invention can be used with other types of medical procedures where suction is to be applied to the stomach or a fluid introduced into the stomach The system 20 comprises a flexible sizing tube 22, a valve 24 and a perforated tip 26. In FIG. 11 there is shown an alternative and preferred sizing tube 122. In both embodiments the sizing tube 22 and 122 is an elongated flexible member having a central passageway 22A (FIGS. 1 and 3B) formed, e.g., extruded, of any suitable material. One particularly suitable material is a second generation styrenic block copolymer with a hydrogenated midblock of styrene-ethylene/butylene-styrene (SEBS) or styrene-ethylene/propylene-styrene (SEPS), such as sold by Kraton Performance Polymers, Inc. under the trade designation Kraton grade G2705.

The sizing tube 22 and 122 is somewhat long, e.g., approximately 76 cm, so that it can be extended through a patient's mouth into the patient's stomach and preferably comes in plural sizes, with the appropriate size being selected for the particular patient to form a desired size stomach. For example, the outside diameter of the sizing tube may be available in 32, 36 or 40 French sizes, while the inside diameter (i.e., the diameter of passageway 22A) is approximately 0.200 inch to 0.25 inch (depending on the outside diameter of the sizing tube). The sizing tube may include indicia or markings 22B at 30, 40 and 50 cm on its outer surface measured from its distal end to provide the user with information as to the depth that the sizing tube has been inserted into the patient's stomach. That indicia may be pieces of suture inserted into the wall of the sizing tube after it has been extruded. Alternatively, the indicia may be molded into the sizing tube (e.g., be in the form of a short section of suture molded into the material making up the sizing tube) or may be applied (e.g., printed) on the outside of the tube if suitable.

Figure 12:
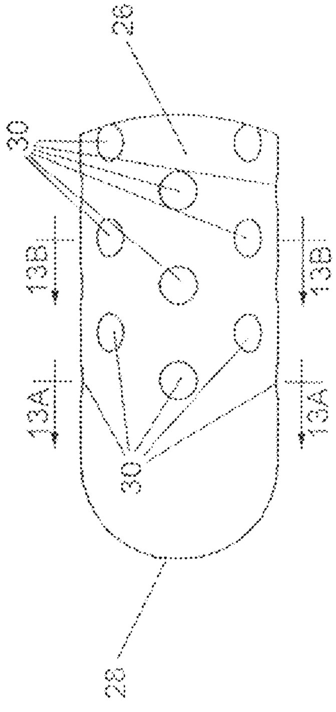
FIG. 12 is an enlarged view of the distal portion of the sizing device shown within the circle identified by the letter "A" in FIG. 11.

The perforated tip 26 of the sizing tube 22 and 122 is located at the distal end 28 and comprises a plurality of small apertures 30 extending through the side wall of the tube 22 and in fluid communication with the tube's central passageway 22A. The central passageway extends the entire length of the tube 22 and 122 from its proximal end 31, at which the valve 24 is located to the distal end 28 of the tip 26. As best seen in FIGS. 1, 11 and 12, the distal end 28 of the tip 26 is closed and is rounded, e.g., of hemispherical shape.

The valve 24 is in the form of a two-position vented slide valve. The slide valve includes a body 32 having a first coupling 34 which is tubular and arranged to be disposed (e.g., frictionally fit) within the hollow proximal end 30 of the sizing tube 22. The body 32 includes a second coupling 36 which is also a tubular member. The two couplings 34 and 36 are axially aligned with each other and project radially outward from diametrically opposed locations on the body 32 of the valve. The body 32 is a hollow member in which a slide 38 is disposed.

The slide 38 is arranged to be slid into one of two positions to cause the valve 24 to be in either an open ("on") position or a closed ("off") position. To that end, the slide 38 is a hollow tubular member having a first end cap or head 38A at one end thereof and a second end cap or head 38B at the opposite end thereof and a pair of diametrically aligned openings (not shown) located in the side wall of the slide half way between the heads 38A and 38B. Each of the openings is of approximately the same internal diameter as the internal diameter of the couplings 34 and 36. When the slide 38 is in the position shown in FIG. 2 the valve is in its open or on position, whereupon the openings (not shown) in the slide 38 are aligned with the hollow interior of both of the couplings 34 and 36 thereby providing a fluid path therethrough. However, when the slide is in the position shown in FIG. 1 the valve is in its closed or off position, whereupon the openings (not shown) in the slide 38 are not aligned with the hollow interior of both of the couplings 34, so that respective portions of the side wall of the slide block the interior of the two couplings 34 and 36, thereby isolating the coupling from each other.

Figure 2:
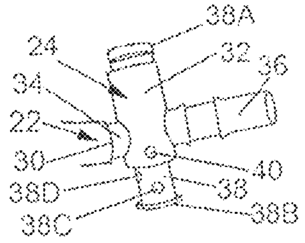
FIG. 2 is an isometric view of the valve shown in FIG. 1 in its open or "on" position.

As mentioned earlier the valve 24 is vented. To that end, the slide 38 includes a pair of apertures 38C and 38D (FIG. 2). Aperture 38C is disposed in the side wall of the slide 38 adjacent the cap 38B, whereas aperture 38D is disposed in the sidewall slightly inward of the aperture 38C and approximately 90 degrees from it. The body 32 includes an aperture 40. The aperture 40 along with aperture 38C serves as a vent for the valve when the valve is in its "off" or closed position. In particular, when the head 38B of the slide is pushed inward so that the slide is in the position like shown in FIG. 1, the aperture 38C of the slide will be aligned with the aperture 40 of the valve's body and the aperture 38D will be aligned with the hollow interior of the coupling 34. Accordingly, ambient air can flow through aligned apertures 40 and 38C into the interior of the slide and from there through aperture 38D into the interior of the coupling 34. Hence the interior of the sizing tube 22 will be at atmospheric or ambient conditions when the slide switch is in the closed or off position.

Figure 8:
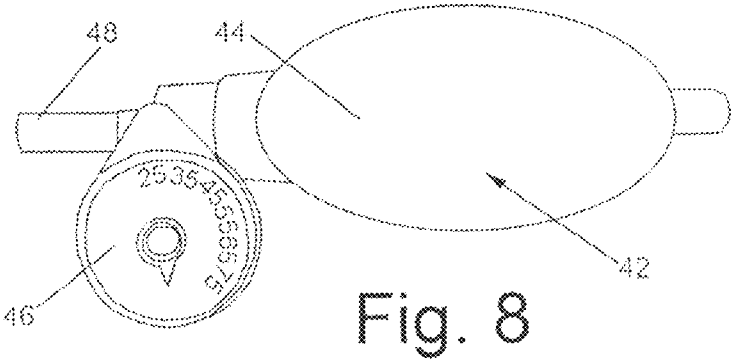
FIG. 8 is a plan view of a pumping device which is arranged to be used with the sizing device to pump a fluid, e.g., air, some other gas or liquid, into the stomach of the patient.

The coupling 36 is arranged to be selectively connected to a source of suction, e.g., a suction tube connected to a hospital's wall suction line (not shown), when suction is to be applied via the instrument to the stomach of the patient, or to a hand pump assembly 38 (FIG. 8), which will be described later, when a fluid, e.g., air, is to be applied into the patient's stomach. The coupling 36 is tubular and arranged to be disposed (e.g., frictionally fit) within either the hollow end of a suction tube connected to a source of suction or to a coupling (to be described later) forming a portion of the pump assembly 42 shown in FIG. 8. The source of suction may be a wall suction line that is typically provided in a hospital.

The pump assembly 42 is used to pump air or some other gas or liquid into the patient's stomach via the instrument 22 for reasons to be discussed later. The pump assembly 42 basically comprises a manually compressible bulb 44, an associated pressure indicator 46 or gauge and an adapter 48. The bulb 44 is arranged when squeezed to force any air within it out through an outlet port and into the adapter 48. The adapter 48 is arranged to be connected to the coupling 36 to releasably connect the pump assembly to the instrument 22. The bulb includes an inlet port through which air passes when the bulb is relaxed. The pressure gauge 46 is coupled to the outlet port of the bulb to provide an indication of the level of air pressure produced by squeezing the bulb. The pressure gauge typically indicates pressures in the range of 0-100 mmHg.

Figure 3A:
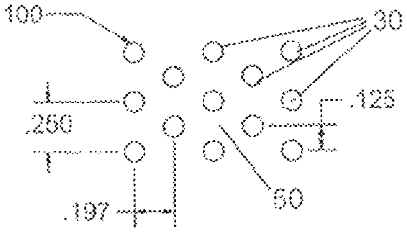
FIG. 3A is an enlarged plan view showing the spacing of a portion of the apertures located in the distal end of the device shown in FIG. 1.

The details of the apertures 30 will now be described with reference to FIGS. 1 and 3A. The apertures 30 are of a constant diameter along their entire length, are small in size and are arranged in a symmetrical array 50 about the periphery of the distal end portion of the sizing tube closest to the distal or free end 28. The spacing between the apertures 30 in the array portion 50 is shown in FIG. 3. However, in the area of the sizing tube 22 just proximally of the symmetric array 50, the apertures 30 are disposed in a helical or spiral configuration 52, with the spacing between adjacent apertures in the spiral configuration being greater than in the array 50, yet still equidistant. There are more apertures in the array area 50 to provide increased flexibility to the distal end of the sizing tube, so that it can be more easily directed to the appropriate location in the stomach. Typically this is done with laparoscopic graspers. In the area 52 the apertures are more spread out allowing suction to be applied at those portions of the tube. However, since they are spread out the tube is stiffer at this location. Having the tube be appropriately stiff is important because it has to be inserted in the patient's mouth adjacent a breathing tube, through the upper esophageal sphincter, through the esophagus and then through lower esophageal sphincter into the stomach.

It should be pointed out at this juncture that there are a sufficient number of apertures extending about the periphery of the sizing tube and along a substantial portion of the length of the sizing tube to ensure that when suction is applied the sizing tube is held in place by the suction and a clear line of delineation or demarcation of the sizing tube within the stomach is achieved (as will be described later).

The following constitutes various preferred exemplary diameters of the apertures 30. In particular, a preferred range of diameters for each aperture 30 is 0.05 inch to 0.25 inch, more preferred range of 0.030 to 0.200 inch, with the most preferred aperture diameter range being 0.07 inch to 0.15 inch. Thus, an embodiment of this invention can make use of apertures 30 of approximately 0.10 inch, whereupon the area of a single aperture is approximately 0.008 square inches.

Figure 3B:
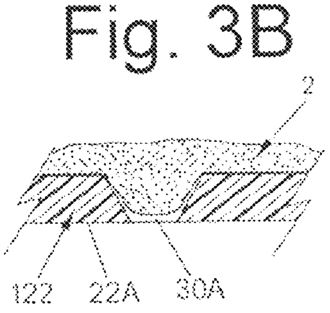
FIG. 3B is a cross sectional view of the shape of a typical preferred aperture, i.e., a flared aperture, for sizing instruments constructed in accordance with this invention.

It should be pointed out at this juncture that the apertures 30 need not be of a constant diameter. In fact, it may be desirable to make use of apertures that are flared so that the diameter of each of the apertures on the outer surface of the sizing tube is larger than the diameter of the apertures on the inner surface of the sizing tube. Such an arrangement is shown in FIG. 3B. The apertures 30A should facilitate the release of the sizing tube from the gastric tissue 2 when such action is desired since gastric tissue can more readily pull out of a flared hole 30A than a straight hole 30 or an inwardly tapered hole. For a 36 French sizing tube 122 the diameter at the outer end of each aperture 30A is approximately 0.11 inch, while the diameter at the inner end of each aperture 30A is approximately 0.08 inch and the thickness of the wall of the sizing tube is approximately 0.13 inch.

In the illustrated embodiment of FIG. 1 there are seventy-two apertures 30 in the first 2.5 inches of the length of the sizing tube 22, starting at its distal end, and sixteen apertures in the next 3.5 inches of the tube's length for a combined total of eighty-eight apertures. Another embodiment (FIG. 11) contemplated is a sizing tube including one hundred fifty-two apertures 30, each of a diameter of 0.10 inches and spread out uniformly in an array over the first five inches of the sizing tube's length.

In FIG. 11, an alternative sizing tube with a different configuration of aperture 30 is shown and will be described in detail later.

When a sizing tube constructed in accordance with any embodiment of this invention is in place in the stomach and suction applied, the applied suction creates a force that holds the sizing tube at that position. During laparoscopic surgery air pressure is used to inflate the abdominal cavity in order to provide an internal work space. Typically this air pressure is in the range of 0.1-0.4 psi. Suction applied to the sizing tube creates a negative pressure within the sizing tube and at the tube's apertures. The resulting force holds the sizing tube in place and anchors it to the stomach wall. This force is a function of: (1) the differential pressure between the abdominal cavity and the sizing tube and (2) the combined area of the apertures. For example, a sizing tube with eighty-eight apertures, each of a diameter 0.10 inches, equals an area of 0.7 square inches. With a positive pressure of 0.2 psi in the abdominal cavity and a negative pressure of 1.5 pounds (78 mm HG) in the sizing tube there is a differential pressure of 1.7 psi. The force is equal to 0.7 square inches X 1.7 psi or 1.2 pounds. It is preferred that the force holding the sizing tube in position be in the range of 0.1 to 200 pounds, more preferably between 0.3 and 20 pounds and most preferably between 0.5 and 8 pounds.

The force applied to the stomach by the sizing tube with suction applied may also be considered independently of the positive pressure that is applied within the peritoneal cavity to facilitate laparoscopic surgery. As such, the suction force is the aperture area multiplied by the applied suction pressure. For example, if there are eighty-eight (88) apertures with a diameter of 0.1 inches, the aperture area is 0.7 square inches. With suction applied at a level of 2.4 psi (125 mmHg) the suction force applied by such a sizing tube is 0.7 square inches times 2.4 psi=1.7 pounds. That suction force is merely exemplary of many suction forces that are contemplated by the subject invention. To that end, a preferred range of suction force applied is 0.05 to 200 pounds, with a more preferred range being 0.1 to 100 pounds, and an even more preferred range being 0.3 to 20 pounds. The most preferred range is 0.5 to 8 pounds.

The suction force per unit length applied at the apertured portion of the device is another important parameter of the invention. For example, if there are one-hundred-fifty-two (152) apertures each with a diameter of 0.1 inches spread across a five (5) inch long longitudinal section of the sizing tube, the aperture area is 1.2 square inches. With suction applied at a level of 2.4 psi (125 mmHg) the suction force applied is 2.9 pounds. Thus the suction force per unit length applied at the apertured portion is 2.9 pounds divided by 5 inches or 0.58 pounds per inch length. That suction force per unit length is merely exemplary of many that are contemplated by the subject invention. To that end, a preferred range of suction force per unit length is 0.02 pounds per inch length to 21 pounds per inch length, with a more preferred range from 0.1 to 10 pounds per inch length, and with the most preferred range is from 0.2 to 5 pounds per inch.

As should be appreciated by those skilled in the art the distal end portion of the sizing tube 22 encompassing the array 50 of apertures will be subject to some degree of longitudinal collapse due to the multitude of apertures in that portion of the sizing tube. Thus, to prevent such collapse, which could be detrimental to the placement of the sizing tube within the patient's stomach, a helical anti-compression spring (not shown in FIG. 1 but shown in FIG. 11 and which will be described later) may be located within the distal end of the sizing tube in the area making up the array of apertures.

Turning now to FIGS. 4-7 the use of the systems of this invention will now be described. To that end, the distal end 28 of the sizing tube 22 or 122 is introduced through the patient's mouth and down through the patient's esophagus 10A into the interior of the patient's stomach 10B. The presence of the multiple apertures 30 in the distal end of the sizing tube renders that end quite flexible to facilitate the placement of it in the patient's stomach. If it is desired to "decompress" the patient's stomach (e.g. remove air from the stomach) or to remove any liquid from the stomach, the instrument 22 is attached via its coupling 36 to a suction line connected to a source of suction, e.g., a hospital wall suction line. The amount of suction provided may be controlled by use of the devices disclosed in U.S. Letters Pat. Nos. 5,992,239 and 7,686,785, which are assigned to the same assignee as the subject invention and whose disclosures are incorporated by reference herein. The slide 38 of the valve 24 can then be moved to the open or on position. In particular, the user presses on the head 38A of the slide to move the slide to the position shown in FIG. 2, whereupon the ports in the side wall of the slide are aligned with the passageways through the couplings 34 and 36 so that suction will be applied down the interior of the sizing tube 22 and out through its apertures 30 to draw air and/liquid out of the stomach through the instrument 22.

Figure 4:
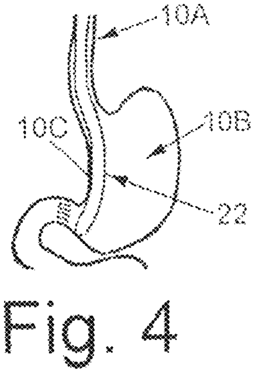
FIG. 4 is an illustration showing any of the sizing instruments of this invention being used to perform a sleeve gastrectomy, wherein the instrument is shown at its desired position within the stomach of the patient.
Figure 5:
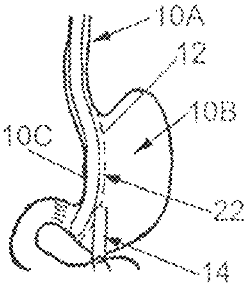
FIG. 5 is an illustration, similar to FIG. 4, but showing the stomach being resected by a conventional cutter/stapler device along a line parallel to the sizing device of this invention.

If after such decompression/stomach evacuation procedure has been accomplished (or if no such procedure has been accomplished), if it is desired to perform a sleeve gastrectomy procedure on the patient, the distal end of the instrument should be moved to the position shown in FIG. 4, if it is not already in that position. In that position the distal end of the instrument is located against the lesser curvature 10A of the stomach. If the valve 24 is not in the open position, its slide can be moved to that position to couple the source of suction to the sizing tube. The suction serves to hold the distal end of the instrument in position in the stomach and brings adjacent portions of the stomach into close engagement with the periphery of the distal end portion of the instrument. This action provides the surgeon with a clear line of delineation or demarcation of the instrument within the stomach, which can be readily seen by the surgeon via a laparoscope. In FIG. 5 this line of demarcation showing the position of the instrument in the stomach is represented by the broken line 12. The level of suction to be applied is typically in the range of 25-200 mm Hg, most preferably 50-150 mm Hg, but could be in the range of 1 mm Hg to 700 mm Hg.

Figure 6:
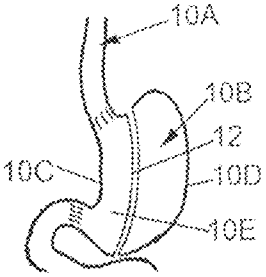
FIG. 6 is an illustration, similar to FIGS. 4 and 5, showing the stomach after a portion has been resected therefrom.
Figure 7:
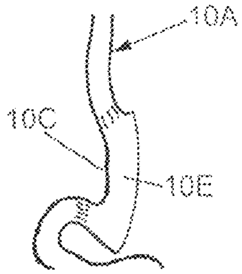
FIG. 7 is an illustration, similar to FIGS. 4-6, showing the residual portion of the patient's stomach after a portion has been resected therefrom and removed laparoscopically, thereby leaving the patient with a much smaller stomach.

The outer diameter of the instrument (sizing tube) used, e.g., whether 32, 36 or 40 French, is selected so that when the adjacent portions of the patient's stomach are brought into engagement with the distal end portion of instrument by the suction that distal portion of the instrument defines or establishes the size to which the patient's stomach is to be reduced. Accordingly, the surgeon can then use a conventional resecting stapler 14 or other conventional instrument to resect the stomach along, i.e., closely parallel to, the delineation line 12 to cut away a major portion 10D of the patient's stomach as shown in FIG. 6, with the marginal edges of the remaining stomach being stapled or otherwise joined along a seal line, thereby leaving the patient with a reduced size or residual stomach 10E as shown in FIG. 7.

In accordance with one preferred methodology of this invention, the seal line extends at least 0.5 cm (more preferably 1.0 cm) from said delineation line on the opposite side of the delineation line from the position of the sizing tube in the vicinity of the gastric esophageal junction (GEJ) and the Angle of HIS in order to minimize the chance of leakage along the seal line in that region. Thus, if the seal line is to be accomplished by use of a resecting stapler, the staple line should be laterally to the fat pad at the GEJ away from the delineation line to avoid stapling onto the GEJ and consequently prevent leaks.

Moreover, the seal line should not compromise the width of the residual portion of the patient's stomach (the "sleeve") near the incisura angularis. In this regard it is important that there is no further narrowing or obstruction of the gastric outlet or body of the stomach, since that action may result in or perpetuate a proximal staple line disruption. To that end, it is suggested to start 2 cm to 6 cm from the pyloris and to angle the stapler to prevent narrowing at the incisura angularis. In addition, it is suggested that the seal line be formed at least 0.5 (more preferably 1) cm from the delineation line on the opposite side of the delineation line from the position of the sizing tube in the vicinity of the incisura angularis to reduce the chance of the formation of a stricture thereat.

After the sizing procedure has been accomplished, the integrity of the patient's reduced size (residual) stomach 10E can then be checked for leaks. In particular, the suction tube from the source of suction may be disconnected from the coupling 36 while the valve 24 is in its open state or else the valve may be moved to the closed state by pushing on the cap 38B to the position shown in FIG. 1. In either case this action removes suction from the interior of the sizing tube and allows the sizing tube to vent, to enable any residual suction or pressure within the stomach to equilibrate to ambient atmospheric levels. The pump assembly 42 may then be connected to the instrument and the slide of the valve 24 moved to the open or on position, if it is not already in that position. At this point the user can manually squeeze the bulb 44 to force air from the bulb 44 into the instrument 20 down through the sizing tube 22 and out through the apertures 30, thereby insufflating the stomach to a desired pressure. That pressure is indicated on the pressure gauge 46. At the same time that the bulb is being squeezed to pressurize the stomach saline solution can be applied to the outer surface of the stomach along the suture/staple line. Thus, if there are any leaks, air bubbles will be produced at the site of the leak(s), which can be readily observed by the surgeon via the laparoscope. Alternatively, a leak test can be performed by merely opening the valve 24 and introducing a suitably colored liquid, e.g., saline solution with methylene blue dye, through the instrument into the stomach of the patient. Any leak will be readily observable via the laparoscope by the egress of blue dyed saline through the leak site(s).

During bariatric surgery it is necessary to mobilize the greater curvature of the stomach by separating it from the omentum and other parts of the anatomy where it is connected. This requires manipulation of the stomach and lifting the lesser curvature. After mobilization the stomach may be less spread out than before mobilization resulting in bunching and folding of the stomach. In such a case, once the sizing tube of this invention is in place and suction applied it may be difficult to determine exactly where the sizing tube is as the folds of the stomach might make it harder to discern the precise position of the sizing tube or if the fold(s) is/are large enough such fold(s) could appear to be the sizing tube itself. Accordingly, to overcome the problem of stomach bunching, should it occur during a sizing procedure, the application of suction, if applied, should be discontinued. Then air or saline should be introduced into the stomach via the sizing tube to expand the stomach and thereby “unfold” it. Once that has been accomplished the air or saline can then be removed by reapplying suction to thereby decompress the stomach and provide proper delineation of the sizing tube.

It should be pointed out at this juncture, that in lieu of the components described above, the system can be configured with the sizing tube, hand pump and suction connector and a selector valve all integral, allowing the user to select between the three functions of suction, inflation and vent.

Other sources of suction can be used in place of the suction source typically found in a hospital. For example it is contemplated that a system constructed in accordance with this invention may include a portable pump having a suction controller to be able to provide suction levels up to 700 mm Hg vacuum. In U.S. Pat. No. 7,857,806, whose disclosure is incorporated by reference herein, there is disclosed a portable pump which can be modified for use with the subject invention. In typical operation of a gastric sizing tube of this invention the level of suction applied is approximately 100 mm Hg vacuum. However, it is desirable to go as high as 700 mm Hg to increase securement force and delineation. This level of suction can be considered safe when it is only being applied for a short period of time. It is also desirable that the source of suction have good flow. In many cases, the lower esophageal sphincter and/or the upper esophageal sphincter seal around the gastric sizing tube. Sometimes, it is possible that a seal may not exist or be very good because the sphincters are relaxed or open. In such a scenario air would flow into the mouth and then into the sizing tube. A suction source with good flow capacity should overcome any such air leaks. It is believed that adequate flow output is at least 1 LPM at 100 mm Hg vacuum. A higher flow rate, e.g., 10 LPM at 100 Hg would likely be better.

It should be pointed out at this juncture that at the beginning of the sleeve gastrectomy procedure the sizing tube is placed in the stomach as described above. Some clinicians do this before establishing pneumoperitoneum and laparoscopic visualization, while others do this after establishing pneumoperitoneum and laparoscopic visualization. Once the sizing tube is placed in the stomach, suction is applied to decompress the stomach by removing air and liquid that is in the stomach. To that end, some clinicians like to move the sizing tube around to various parts of the stomach with suction applied in order to be certain that all stomach contents have been removed. After decompression of the stomach the sizing tube can be moved to the lesser curvature of the stomach and suction applied to secure the sizing tube in position and to create a visually perceptible line of demarcation, such as described previously. Prior to sizing and resecting the stomach there are a number of other preparatory surgical steps such as dissecting the greater curvature of the stomach from the omentum, dissecting and sealing the blood vessels of the greater curvature, etc. These steps are typically done after decompression of the stomach but before sizing of the stomach sleeve. They can be done with the sizing tube secured against the lesser curvature or with the sizing tube at another location within the stomach. Ultimately, prior to sizing and resecting the stomach the sizing is placed against the lesser curvature with suction applied to secure the device and provide the visually perceptible line of demarcation.

Using the visual demarcation line, the stomach can be resected with a cutting stapler that simultaneously seals and cuts the stomach into the correct shape. Typically the stapling follows the demarcation line and because the line of demarcation is clear the stapler can be positioned slightly away from the demarcation line, such as at the incisura anuglaris and the gastroesophageal junction, as described above. After the stomach has been sized, some surgeons perform a leak test, which can be performed as also described above.

Turning now to FIGS. 9 and 10, the details of an alternative system 120 will now be described. The system 120 makes use of a sizing tube or instrument 22 or 122 and valve 24 like those described above plus the addition of an integrated suction controller or regulator 200. In the interest of brevity the components and features of the system 120 that are the same as the system 20 will be given the same reference characters and the details of their construction, arrangement, function and operation will not be reiterated.

As can be seen in FIG. 9 the integral suction controller 200 is positioned between the sizing tube 22 (or 122, as the case may be) and the valve 24. Alternatively, it may be positioned connected to the valve, so that the order of components is as follows: sizing tube 22 (or 122), valve 24 and controller 200. The suction controller serves to ensure that a desired level of suction is applied to the sizing tube 22 (or 122) when the valve 24 is open to ensure proper and safe operation of the sizing tube. The suction controller 200 has a suction source side which is designated by the reference number 201 and is arranged to be connected to a source of suction such as a hospital's wall suction line, with the valve 24 interposed therebetween. The coupling 36 of the valve 24 is connected to a conduit or suction line 122 which is in turn connected to some source of suction (e.g., the hospital wall suction line—not shown). The opposite side of the controller 200 is designated by the reference number 202 and is arranged to be connected to the proximal end 31 of the sizing tube 22.

The controller 200 is housed within a hollow housing 203, which includes a cover 204. The housing and the cover are each formed of a rigid plastic, such as ABS. A piston 205 is disposed within the housing and is also formed of a rigid plastic, such as ABS. The piston includes a top portion 206 which extends through an opening 210 in the cover. The space between the outer periphery of the top portion 206 and the opening 210 forms a vent or port to the ambient atmosphere so that the chamber 213 will be at the pressure of the ambient atmosphere.

A spring 207 is located within the housing under the piston 205 and serves to bias the piston upward in the housing. The spring is formed of any suitable material, e.g., stainless steel. A rolling diaphragm 208 is coupled to the piston 205 and the housing 203. Diaphragm 208 is engaged in a sealing fashion between housing 203 and cover 204. The diaphragm can be formed of any suitable material, e.g., Nitrile. A seal 209 is located on the underside of the piston and is arranged to engage a seat 215 when excess suction is applied (as will be described later). The seal is formed of any suitable material, e.g., silicone rubber. The interior of the housing just below the cover 204 and above diaphragm 208 forms a first chamber 213, while the portion of the housing below the diaphragm forms a second chamber 214, with the diaphragm isolating the two chambers from each other. The seat extends about the periphery of the conduit 211.

Operation of the controller 200 is as follows. Suction is applied from the suction source (not shown) through the open valve 24 and into a conduit 211 at the suction side 201 of the controller and to the patient side 202 via the conduit 212. The proximal end 31 of the sizing tube 22 is connected to the conduit 212, so that suction is delivered to the sizing tube and subsequently to the patient. The controller 200 is configured to limit the amount of suction applied to the patient to a predetermined, desired level, even if a suction level greater than the predetermined level is applied via that conduit 211 from the suction source. The predetermined or desired suction level is established by the spring 207 and dimensions of the housing 203, the piston 205 and the seal 209. In this regard the pressure within chamber 213 will be equal to atmospheric pressure by virtue of the communication of the chamber 213 with the ambient atmosphere via the vent 210. With suction applied, the pressure differential between the chambers 213 and 214 forces the diaphragm 208 and the piston 205 downward toward the seat 215 of the housing 203 against the bias of the spring 207. If the suction applied via conduit 211 is greater that the predetermined level the piston 205 and diaphragm 208 will move such that the seal 209 on the bottom of the piston comes into engagement with the seat 215 thereby isolating chamber 214 from the vacuum source. This action thereby limits the level of suction in chamber 214 and ultimately at the patient to the predetermined level. If, however, the suction applied via conduit 211 is less than the predetermined level the piston 205 and diaphragm 208 will only move part of the way downward. As such the level of suction applied to conduit 211 will equal that in conduit 212 and that applied to the patient.

The controller 200 is arranged to provide an indication as to whether or not the suction applied is equal to or less than the predetermined, desired, level. Thus, the top surface of the portion 206 of the piston 205 is in the form of a colored tape 206A. The color of the tape is selected to provide a distinctive appearance from the rest of the piston, e.g., the periphery of the top portion 206. For example, in a preferred embodiment the tape 206A at the top portion 206 of the piston is colored white, while the remainder of at least the top portion 206 of the piston, if not the entire piston, is colored red. The cover 204 is preferably the same color as the tape 206A, e.g., white, or some other color that will readily contrast with the color of the top surface (i.e., the tape 206A) of the piston. The choice of a contrasting appearance, e.g., color, of the piston from the appearance of its tape top surface and the cover serves to facilitate visualization of the level of suction applied. For example, when the suction level in chamber 214 has not reached the predetermined, desired level the top portion 206 of the piston 205 will protrude above the top surface of the cover 204 and a red band (the periphery of the top portion 206) will be readily visible. When the level of suction in the chamber equals the predetermined set point (i.e., the desired level) the piston 205 will be at or below the surface of the cover 204 and the red band will not be clearly visible.

Turning now to FIGS. 9A and 10A there is shown an alternative suction controller or regulator 300 constructed in accordance with this invention and forming a portion of an alternative preferred system of this invention. The controller 300 is constructed similarly to the controller 200 except that it does not include any mechanism for indicating the level of suction applied. It does, however, include structure (to be described shortly) which ensures that the upper chamber 213 is always at atmospheric pressure. In addition, it includes means to prevent the piston 205 from becoming stuck for an extended period of time on the seat 215 in the event of what will be referred to hereinafter as an over-travel situation. Since many of the components of the controller 300 are also found in the controller 200, in the interest of brevity the common components of the controller 300 with the controller 200 will be given the same reference numbers and the details of the structure, arrangement and operation of those components will not be reiterated.

As can be seen in FIGS. 9A and 10A, the cover 204 includes a hole or port 302, which will be referred to as the atmospheric reference port. The port 302 extends through the thickness of the cover and is in fluid communication with the interior of upper chamber 213 to maintain that chamber at atmospheric pressure. Inasmuch as the port 302 is located in the top surface of the cover, it is susceptible to being blocked or covered by a sticker, some other object or even the finger of a user. To prevent such an occurrence the cover 204 includes structure to prevent blockage of the port 302. In particular, the cover 204 includes a thickened portion 304 located adjacent the port 302 with an elongated shallow slot 306 extending through the thickened portion 304. The outer or top end of the atmospheric reference port is located at the bottom of the slot 306 and is in fluid communication therewith. Each end of the slot is open. Thus if something should be on the top surface of the thickened portion 304 of the cover 204 disposed over the port 302 air can still enter into the port via either open end of the slot.

It has been determined that if the controller 300 is operated in a manner such that a high level of suction is applied very rapidly, the piston 305 may experience an over-travel wherein it moves downward very quickly such that the seal 209 on the underside of the piston becomes stuck on the seat 215. Under this condition the line 212 to the patient would have a higher level of vacuum than the controller was set to provide. The controller could stay in that state for an extended and indefinite period of time, particularly if the apertures 30A in the sizing tube 22 are blocked, e.g., are in tight engagement with the surrounding gastric tissue or are otherwise blocked. To prevent such an occurrence, the controller 300 includes two bleed holes. In particular, as can be seen in FIG. 10A the diaphragm 208 includes a bleed hole 308 in the central portion thereof. The piston 205 of this embodiment is somewhat different in construction than the piston 205 of the controller 200 in that it includes a hollow portion defined by a side wall 310. The sidewall 310 includes a bleed hole 312 extending radially therethrough. Thus, the interior of the hollow portion of the piston 205 is in fluid communication with the lower chamber 214 via bleed hole 312. Since the diaphragm 208 includes the bleed hole 308, which is in communication with the upper chamber 213, that chamber will be in fluid communication with the lower chamber via the bleed hole 308. Hence, if the piston should become stuck on the seat, air which enters into the upper chamber 213 via the port 302 can then pass through the bleed hole 308 into the interior of the piston and from there through the bleed hole 312 into the lower chamber 214. The ingress of air into the chamber 214 will decrease the vacuum within the chamber, thus enabling the spring 207 to move the piston 205 upward and off of the seat 215. In accordance with one exemplary preferred embodiment of the controller 300, the bleed hole 308 is approximately 0.1 inch in diameter, while the bleed hole 312 is approximately 0.015 inch in diameter. During typical operation the flow rate of air into chamber 214 via bleed hole 312 is in the range of 10 standard cubic feet per hour (SCFH) or lower.

As best seen in FIG. 10A the underside of the cover 204 includes a disk 314 located thereon. The disk 314 is formed of the same material as the material of the seal 209. The disk 314 serves to seal the diaphragm bleed hole 308 when the piston is in its maximum up position. The seal 314 serves to prevent the ingress of liquid into the upper chamber 213 when the system is being used to determine if the sealed residual portion of the patient's stomach has any leaks. In this regard, as discussed earlier a dyed liquid can be pumped into the patient's residual stomach via the sizing tube. If that procedure is accomplished using a system like the system shown in FIGS. 9A and 10A, the dyed liquid will be introduced into the chamber 214 and from there through line 212 to the sizing tube. Since the diaphragm 208 includes the bleed hole 308, the dyed liquid within the chamber could leak out of the chamber through the bleed hole into the upper chamber 213, but for the presence of the disk 314 preventing that from occurring.

It has been determined that when a gastric sizing tube, like that described above, is in the stomach of a patient, with suction applied, on some occasions the gastric tube may become clogged. In particular, it is suspected that mucosa from the stomach gets pulled into the apertures or perhaps there is some clotted blood in them. When the apertures are significantly clogged, the sizing tube appears to be stuck to the inside of the stomach, even when suction has been turned off and the sizing tube is vented. Such action is concerning if the withdrawal or removal of the "stuck" tube would damage the stomach by pulling on it. Using the bulb 44 to send air pressure into the sizing tube may unclog some of the holes and then air can enter the stomach. Pumping more air into the stomach expands the stomach, separating the inner lining of the stomach from the outside diameter of the tube. As such, the tube is then freed up for removal from the stomach. However, there are some situations in which the apertures cannot be unclogged by just squeezing the bulb as not enough pressure is generated even if the user squeezes really hard and multiple times.

One solution to this potential problem is the addition of at least one one-way valve at the distal portion of the sizing tube. An exemplary embodiment of a sizing tube incorporating a pair of such valves is shown in FIGS. 11 and 12, with each valve being designated by the reference number 122. The sizing tube 122 is similar to the sizing tube 22 described heretofore, except for the inclusion of the one-way valve(s), each of which is designated by the reference number 124, and a spring, which is designated by the reference number 126. In the interest of brevity the common features of the sizing tubes 22 and 122 will be given the same reference numbers and the details of their construction, arrangement and function will not be reiterated. To that end, as can be seen in FIGS. 11 and 12 the spring 126 is located within the distal end portion of the sizing tube 122 and extends from just distally of the distal-most apertures 30 to a point slightly proximally of the proximal-most apertures, e.g., approximately 1 to 1.5 inches beyond the proximal-most apertures. The spring 126 can be formed of any suitable material. One exemplary material is stainless steel 302. In that embodiment the free length of the spring is approximately 5.75±0.25 inches, with an outside diameter of approximately 0.215±0.10 inch, with closed ends, a wire diameter of 0.015 SS±0.001 inch, and with 8 active coils per inch±1.

Each of the one-way valves 124 basically comprises a slit in the wall of the sizing tube 122. The slits are located proximally of the proximal-most apertures 30 so that they do not engage any of those apertures. The slits extend parallel to the longitudinal axis of the sizing tube and are disposed diametrically to each other. Each slit is approximately 0.440±0.60 inch in length, with the opposing edge portions of the sizing tube's sidewall contiguous with each slit being in engagement so that each slit is normally closed as a result of the resiliency of the material making up the sizing tube. In the exemplary embodiment shown the two one-way valves 124 are located in the area encompassed by the internal spring 126, which provides support to the sizing tube to prevent it from kinking or collapsing.

When suction is applied to the sizing tube the valves 124 are normally (automatically) closed. Upon the application of pressure, e.g., the introduction of a fluid, such as air or saline that is pumped into the sizing tube from the bulb 44, the slits open and the fluid is enabled to pass therethrough out of the sizing tube into the patient's stomach.

It should be pointed out at this juncture, that while the embodiment 122 makes use of two one-way valves 124, other arrangements are contemplated. Thus, the sizing tube can make use of only a single one-way valve or more than two one-way valves. Moreover, while each one-way valve being formed of a slit is preferred due to its simplicity other types of one-way valves can be used. For example, the one-way valve could be spring-loaded momentary valve.

Since the one-way valves 124 are configured so that they allow fluid to pass from inside the sizing tube to outside the sizing tube, but not the reverse, the valves do not pull anything in from the patient's stomach, so that they should not get clogged by materials getting sucked into the sizing tube during the application of suction. If the apertures 30 get clogged and the sizing tube gets "stuck" a fluid, e.g., air or saline, can be easily pumped from the bulb 44 into the sizing tube through the one-way valves, thereby expanding the stomach to free the sizing tube so that is no longer stuck. The one-way valves 124 can be operated to pump a fluid therethrough into the patient's stomach before or after the resection of the stomach, depending upon if and when the sizing tube becomes stuck. In fact, if during the bariatric procedure the stomach becomes folded with at least one fold to obscure or interfere with the visualization of a visually perceptible delineation line, the application of suction to the patient's stomach via the sizing tube can be halted, and a fluid, e.g., air or saline, pumped into the patient's stomach via the one-way valves to thereby remove the at least one fold, whereupon suction can be reapplied to the patient's stomach to hold those portions of the patient's stomach in such engagement with the sizing tube to thereby provide the visually perceptible delineation line used to resect the stomach.

Turning back to FIG. 1, it can be seen that the system 20 shown therein (or any system constructed in accordance with this invention for that matter), may include a flow meter 400 to monitor the flow of fluid through the system and thus enable one to infer the level of suction in the distal end of sizing tube. The flow meter 400 may be of any conventional construction, one particularly effective flow meter is that shown in U.S. Pat. No. 7,438,705 (Karpowicz et al.), which is assigned to the same assignee as the subject invention and whose disclosure is incorporated by reference herein. When using this flow meter it may be desirable to have a reservoir or fluid trap between the sizing tube and the flow meter, so that liquid from the stomach does not interfere with the operation of the flow meter.

Figure 13A:
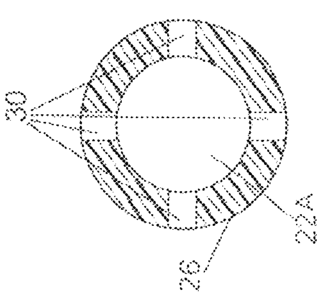
FIG. 13A is a sectional view taken along line 13A-13A of FIG. 12.
Figure 13B:
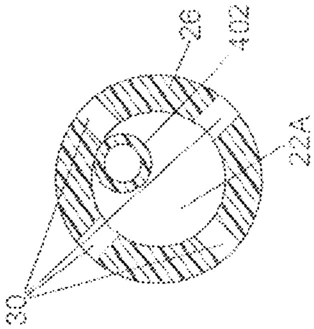
FIG. 13B is a sectional view taken along line 13B-13B of FIG. 12.

As an alternative to use of a flow meter to determine the level of suction within the distal end of the sizing tube, the sizing tube may be constructed to include a passageway or lumen in communication with hollow passageway 22A at the distal end of the sizing tube. Such an arrangement is shown in FIG. 13A. In particular, a lumen 402 extends down through the passageway 22A of the sizing tube 122 the proximal end of the sizing tube to a position ending just before the distal end of the sizing tube. The lumen 402 is open at its distal end. Thus, one can measure the level of suction at the distal end of the sizing tube by coupling a suitable device at the proximal end of the lumen 402.

The lumen 402 can be used for another purpose, in lieu of or in addition to the purpose of determining the level of suction within the distal end portion of the sizing tube. In particular, the lumen 402 can be used to clear the hollow passageway 22A at the distal end of the sizing tube of any secretions, e.g., mucous, which may gain ingress into the sizing tube. That passageway may be connected to a receptacle (not shown) for the collection of such secretions.

A receptacle can also form a portion of any system of this invention to be used to collect any gastric fluids from the patient. In such a case, the receptacle will be coupled to the distal end portion of the sizing tube via any suitable means to enable any gastric fluids drawn into the sizing tube to be carried into the receptacle. That system may also include an overflow detector of any suitable construction to provide an indication that the amount of gastric fluid within receptacle has reached a predetermined threshold, e.g., is about to overflow, and/or to provide a signal to a controller stop to halt the operation of the sizing tube so that no further fluid is drawn into the receptacle until it can be emptied.

As should be appreciated by those skilled in the art, systems and instruments for use in bariatric surgery should provide one or more of the following functions, with the more functions provided the better. They should be constructed for enabling atraumatic insertion into the stomach with a reduced number of insertions and atraumatic removal, with a reduced number of removals. They should enable one to readily decompress the stomach by removing air and other materials. They should enable one to draw stomach tissue together and stabilize and secure the stomach tissue for resection. They should provide sufficient delineation of the stomach tissue to enable accurate resection of the tissue, and minimize risk of accidental stapling. They should enable case of positioning about the lesser curvature of the stomach and also enable one to readily relieve suction periodically to release the stomach tissue for repositioning, if necessary. The suction applying apertures of such systems/instruments should be properly sized to minimize the amount of tissue being drawn into the apertures upon the application of suction. And, they should enable one to infuse fluids into the stomach for various purposes, e.g., leak testing.

The systems and instruments constructed in accordance with this invention meet all of those criteria. In particular, with respect to the matter of atraumatic insertion and removal, it is clear that the sizing tubes of this invention achieve that end by providing a radiused distal end or tip, with the material making up the sizing tube being soft and pliable, and with a smooth exterior surface to minimize friction. Moreover, the sizing tube is sufficiently stiff to enable pushing of it into place through the patient's body, e.g., its apertures are configured and arranged to maintain stiffness parallel to its longitudinal axis. The valve and the suction controller enable the ready application, control and removal of suction. The application of suction facilitates tissue delineation and/or fluid removal. When suction is not applied the sizing tube can readily deliver fluid.

With respect to the function of decompressing the stomach by removing air and other materials from it, the instruments of this invention achieve that end by virtue of the fact that the source of suction can be controlled, with a valve being provided for the application and removal/venting of suction, and with the sizing tube being resistant to longitudinal collapse. Moreover, the sizing tube's apertures are properly sized to maximize fluid and debris removal. For example, the apertures are confined to only the stomach area. Moreover, in one embodiment they exhibit a maximal open area to sizing element total area, e.g., the aggregate area of the apertures is at least 10% of the area of the portion of the sizing tube in which the apertures are located. The array of apertures can be made to extend for at least approximately 1 inches of the sizing tube measured parallel to the longitudinal axis of the sizing tube. Preferably the array extends for approximately 2-5 inches and can extend up to 10 inches. The array of apertures can comprise a first region of at least approximately 2 inches in length measured along the longitudinal axis and wherein the aggregate area of the apertures in the first region is at least 10% of the area of the first region. In addition, the array of apertures can comprise a second region of at least approximately 3 inches in length measured along the longitudinal axis and located proximally of the first region, wherein the aggregate area of the apertures in the second region is at least 2% of the area of the second region. The sizing tube can have an outside diameter of at least 0.375 inch and can be in 32, 36 and 40 French sizes.

With respect to the function of drawing the stomach tissue together and into engagement with the sizing tube to stabilize and secure the stomach tissue for resection, the instruments of this invention achieve that end by virtue of the fact that the apertures are properly sized to minimize tissue trauma, are only in the stomach area, and the suction is controlled. Moreover the instruments include a valve for the application and removal/venting of suction. Moreover, the sizing tubes provide sufficient flow to overcome leaks around the esophageal sphincters and are resistant to longitudinal collapse.

With respect to the function of delineating the sizing tube in the stomach tissue to enable more accurate resection of the tissue and minimize risk of stapling of the sizing tube, the instruments of this invention achieve that end by having apertures of the sizing tube that are properly sized, confining them to the stomach area and having them extend along and about a sufficient length of the sizing tube to ensure than when suction is applied the sizing tube is held securely in place. Moreover, the apertures can be arranged in arrays that are uniform, circumferential and patterned for optimal suction application to draw stomach tissue together and hold the sizing tube in place. The controlled source of suction with sufficient flow acts to overcome leaks around upper and lower gastric sphincters. In addition, the valve serves to enable the application and removal/venting of suction. Relief of suction periodically facilitates the release the tissue for ease in repositioning.

With respect to the function of facilitating the infusion of fluids for various purposes, such as leak testing and unfolding, the instruments of this invention achieve that end by confining the apertures to the stomach area and providing a valve for the delivery of such fluids With respect to the function of enabling ease of positioning about the lesser curvature of the stomach, the instruments of this invention achieve that end by having their apertures patterned and with a density to facilitate flexibility perpendicular to the longitudinal axis of the sizing tube. If desired, a spring may be included in the sizing tube (such as described above) to facilitate flexibility perpendicular to the longitudinal axis of the sizing tube while at the same time preventing longitudinal conduit collapse due to perpendicular flexion. Such action enables the application of uninterrupted suction, or delivery of fluids.

With respect to the function of enabling atraumatic removal and reducing number of removals necessary, the instruments of this invention achieve that end by providing a valve removal/venting of suction and release of tissue. In addition, the apertures are properly sized to minimize tissue being drawn into them and the sizing tube is smooth for minimal friction on tissue.

Systems and instruments that are constructed in accordance with this invention should provide a means to reduce or otherwise solve leakage issues inherent in a sleeve gastrectomy or other a stomach resection procedures. In particular, it is believed that the instruments of the subject invention enable the applied suction to approximate the gastric tissues prior to staple clamping, thus enabling more effective "stress relaxation" of the compressed tissue. Moreover, it is believed that the subject invention reduces need for excess movement of the tissues/repositioning of the stapler. Once the surgeon has properly aligned the instrument with the lesser curvature of the patient's stomach, and the anesthesiologist has applied suction, the suction causes the gastric tissues to wrap around and cling tightly to the sizing tube nearest the lesser curvature, while effectively decompressing and emptying the stomach. The suction enables this positioning to be maintained throughout mobilization of the stomach, inspection of the anterior and posterior aspects of the stomach, as well as during stapler positioning, compression, firing, and removal. Due to this maintenance of positioning, the surgeon is no longer required to constantly pull on, or adjust the gastric tissue around a bougie or within the jaws of the stapler as has characterized the prior art, in order to keep the anterior and posterior aspects aligned properly, to locate the bougie, or ensure adequate compression of the tissue. Reducing the need to pull on and move the gastric tissues reduces the risk of gastric puncture, formation of scar tissue, technical error. Moreover, it may also reduce post-operative gastric inflammation, all of which may otherwise lead to gastric leaks. Reducing the pulling on the tissue may also enable fluid dispersion out of the compressed tissue to be more consistent and regular, resulting in the formation of a more secure seal, e.g., staple, line, and reducing the risk of leaks.

Another advantage of the subject invention is that it should act to prevent stretching of the gastric tissues during and after the procedure. In particular, with the gastric tissues tightly wrapped around the circumference of a sizing tube instrument constructed in accordance with this invention, the gastric tissues should not slide around the instrument. This gives the surgeon confidence in the alignment of the posterior and anterior portions of the stomach along the lateral side of the sizing tube, without excess pulling on the greater curvature of the patient's stomach. This reduced need to pull on the gastric tissues should result in tissue that is less taut and less stressed than can result from prior art techniques. Therefore, the tissue meets with lower-stress compression, resulting in less stress on the staple line, thus reducing the chance of leaks. Reduced stretching of the tissues also reduces the likelihood of technical errors, which may cause a stricture due to uneven stretching of the gastric tissue. As increases in intra-lumenal pressure, and stricture is often associated with leak, the reduction of strictures should also result in a reduction of leaks.

Still another advantage of the subject invention is that the suction produced by the sizing tube clarifies proper staple positioning, thus enabling a more accurate sleeve gastrectomy procedure. In this regard, with the application of suction, the gastric tissue wraps around and clings to the sizing tube. This action causes the remainder of the stomach to lie fairly flat, with a distinct delineation or demarcation line resulting along the lateral side of the sizing tube and marking the outside of the sizing tube. This easily visibly perceived delineation or demarcation line can thus be used as a clear guide for the stapler to follow, enabling a smooth, even staple line closely approximating the sizing tube's calibrated size. A clearly visible line of demarcation also helps to preclude inadvertent stapling of the sizing device such as was common with prior art devices due to an inability to determine the exact location of the devices within the stomach. Following the delineation line, with minimal required tissue manipulation may reduce the amount of staple overlap/crossing, which could otherwise contribute to leaks. The readily visually perceivable delineation line formed by the instrument of this invention is particularly useful for sealing the stomach in the vicinity of the gastro-esophogeal junction GEJ. In particular, the delineation line merges with the outside of the esophagus at the GEJ, enabling a clear identification of the GEJ, and Angle of HIS. This clarity of GEJ identification allows the surgeon to more accurately staple the remaining portion of the stomach without fear of stapling the weaker esophageal tissue.

Figure 14:
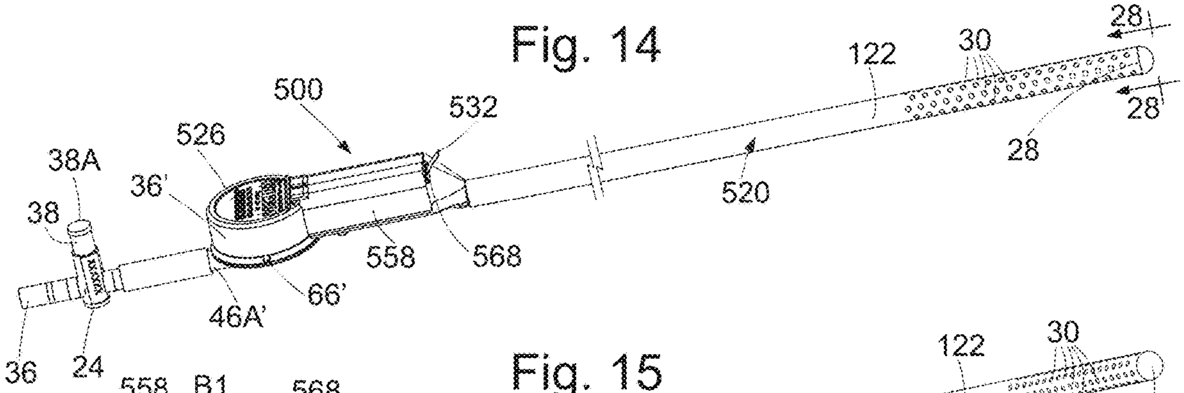
FIG. 14 is an isometric view of another and more preferred exemplary embodiment of a sizing instrument for use in a system constructed in accordance with this invention for gastric and bariatric surgery.
Figure 15:
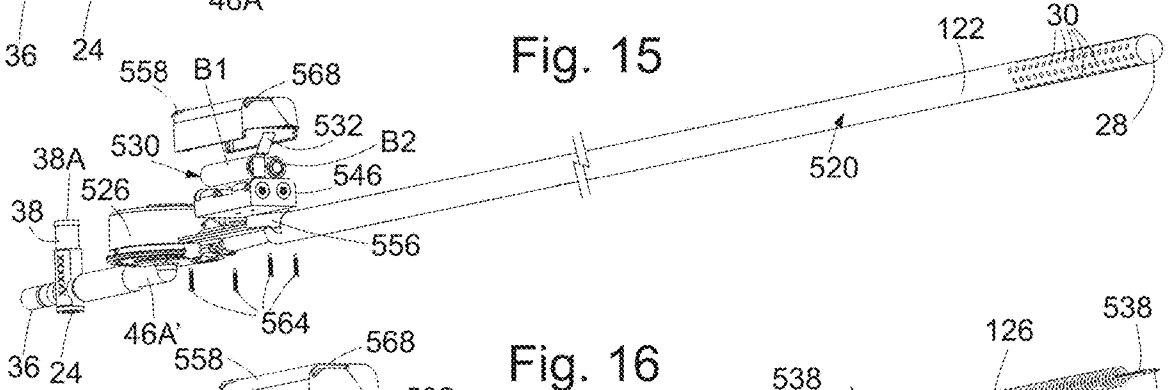
FIG. 15 is an isometric view, similar to FIG. 15, but showing a portion of the instrument, i.e., its electrical power source and the housing thereof, exploded.
Figure 16:
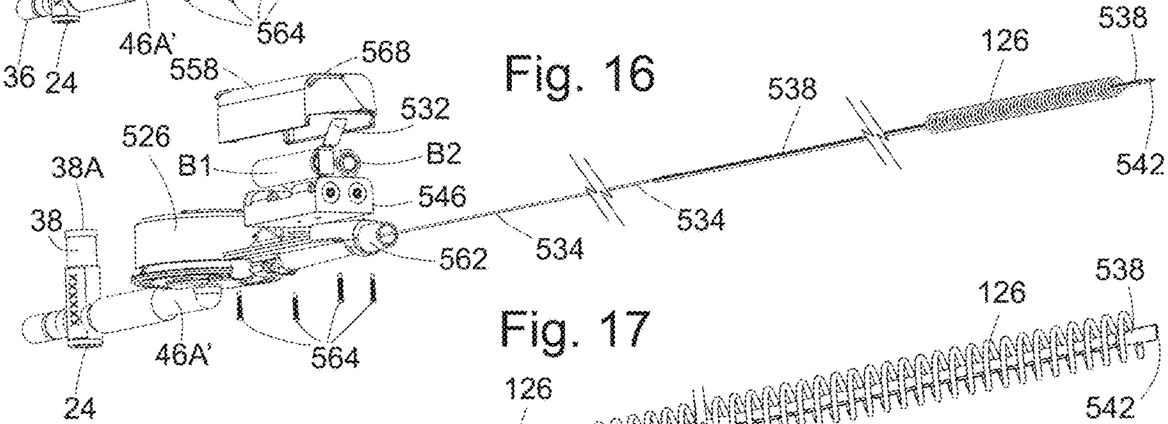
FIG. 16 is an isometric view similar to FIG. 15, but showing the instrument with the sizing tube removed.
Figure 17:
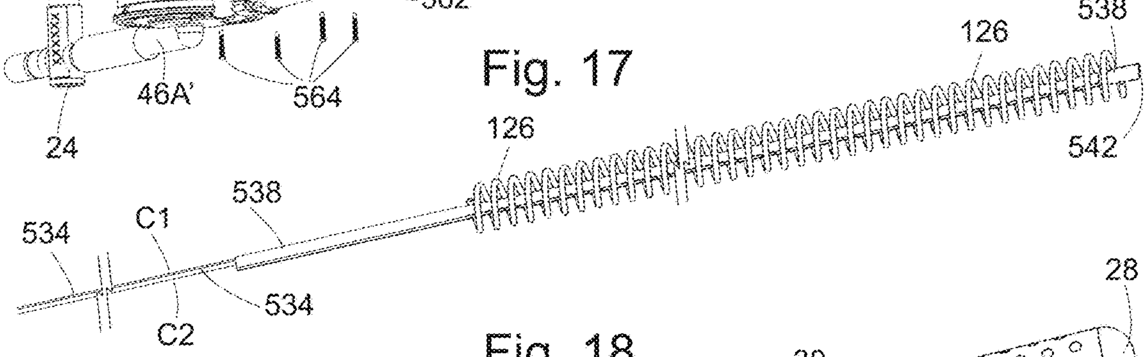
FIG. 17 is an enlarged isometric view of a portion of the helical spring located within the central passageway of the sizing tube and showing a distally located portion of the illumination source of the subject invention located within the helical spring.
Figure 18:
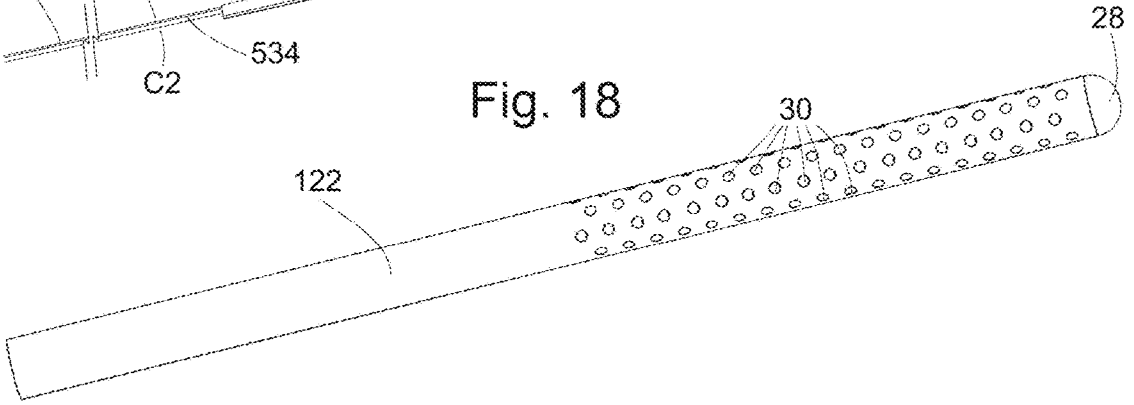
FIG. 18 is an enlarged isometric view of the sizing tube.

Turning now to FIGS. 14-16 there is shown another and more preferred embodiment of a gastric sizing system 500 constructed in accordance with this invention. The system 500 is similar in construction to the systems 20 and 120 described heretofore, except that it makes use of another and more preferred embodiment of an instrument 520 including an illuminated sizing tube 522. The illuminated sizing tube 522 is configured to produce illumination to facilitate its location at any desired position within the patient, e.g., to the position within the patient's stomach along the lesser curvature like described above whereupon controlled suction provided by a suction controller of the instrument can be applied to the interior of the patient's stomach via the array of apertures in the sizing tube. Thus, the instrument 520 includes the heretofore mentioned illuminated sizing tube 522, an electrical subsystem 524, a suction controller 526, and a valve 24. The illuminated sizing tube 522 is composed of a flexible sizing tube 122 like that described above, and a lighting subsystem including an elongated source of illumination 528 (also referred to herein as an elongated light source) located within the central passageway 22A of the sizing tube 122.

Many of the components making up the instrument 520 are similar to the components making up the instruments 20 and 120. In the interest of brevity the common features of the instrument 520 and the instrument 20 and 120 discussed above will be given the same reference numbers and the details of the construction and operation of those common components will not be reiterated.

Figure 19:
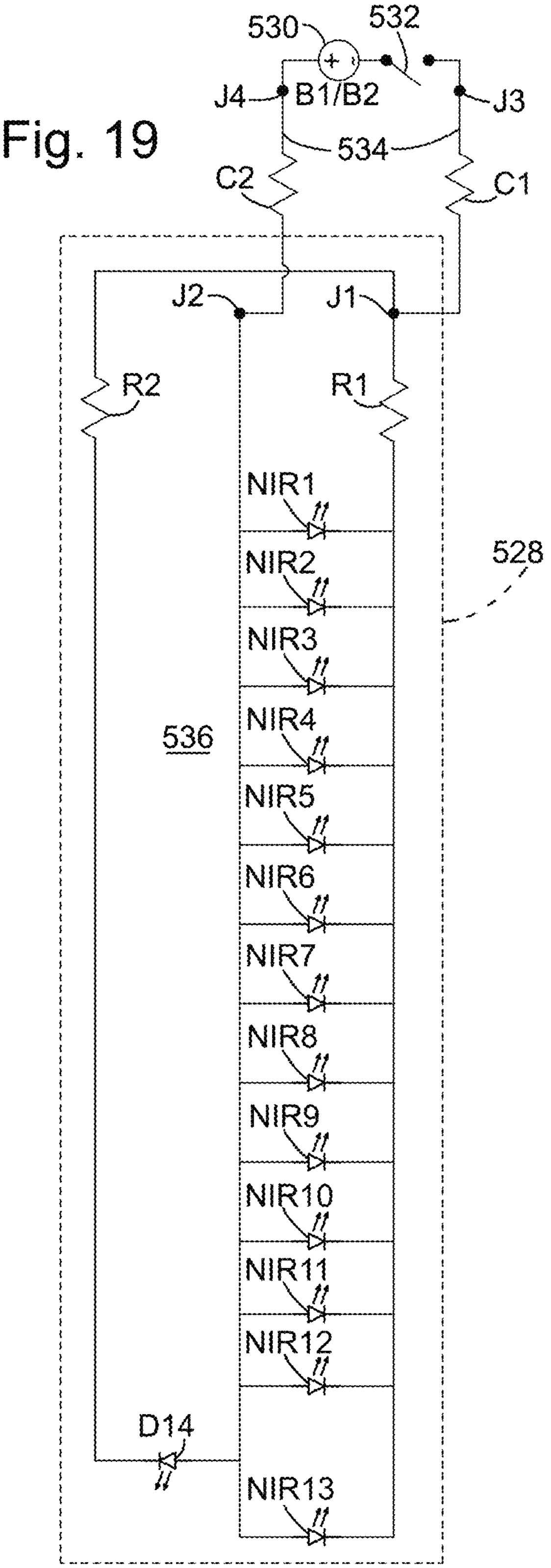
FIG. 19 is a schematic diagram of the electrical components making up the electrical subsystem including an illumination source of the subject invention.

The lighting subsystem, which constitutes a portion of the electrical subsystem 524, is best seen in FIG. 19 and includes an electrical power source 530, a power source actuator 532 (FIGS. 14-16, and 19), and an electrically conductive cable 534 (FIGS. 16 and 19) in addition to the elongated light source 528, all of which will be described in detail later. The electrical subsystem also includes an encasement sleeve 538 (FIGS. 16 and 20) in which the elongated light source is located.

The electrical power source 530 constitutes an assembly which is mounted within a housing (to be described later) on a portion of the suction controller 526. The electrical power source 530 is connected to the elongated source of illumination 528 by the electrically conductive cable 534 and provides electrical power to it. That action causes the elongated light source 528 to produce near infrared (NIR) light within a desired wavelength range that will pass out of the sizing tube and through the wall of the stomach to trans-illuminate the stomach, whereupon the position of the sizing tube within the stomach can be readily detected by the camera of a laparoscope with near infrared laparoscopic imaging capabilities located outside the stomach. Examples of laparoscopic camera systems can be found at various as, but not limited to: websites, such https://en.wikipedia.org/wiki/Indocyanine_green; https://www.intuitive.com/en-us/products-and-services/da-vinci/vision; https://www.stryker.com/us/en/endoscopy/systems/1688-aim-platform.html; and https://www.karlstorz.com/de/en/nir-icg-near-infrared-fluorescence.htm.

Preferably the transillumination intensity is inversely proportional to the thickness of the wall of stomach or other such anatomical structures, and the wall thickness may be used to infer location of internal anatomical features, such as the ridge that may delineate antrum, the lower esophageal sphincter, or cardia at the angle of His. Co-registering internal anatomy of stomach onto its external surface as observed via laparoscope aids in determining optimal stapling trajectory in a given patient, and as such it improves surgery outcomes.

It is preferred (but not mandatory), that the elongated source of illumination (i.e., the light emitting portion of the illuminated sizing tube) extend the length of the sizing tube from it distal end 28 to a proximally located point adjacent the gastroesophageal junction so that the stomach wall adjacent the lesser curvature can be trans-illuminated along its entire length.

In accordance with one aspect of this invention, the intensity of the light emitted from the light emitting portion of the illuminated sizing tube can be increased by including dispersed reflective nano- or micro-particles that increase apparent opacity of the device, by increasing scattering of the incident light. The particles may be titanium dioxide ($TiO_2$), cellulose or similar reflective materials that are easily dispersed in a polymer or in a resin.

As will be described in more detail later in clinical practice a portion of the illuminated sizing tube of the instrument 520 is inserted into the stomach to aid the surgeon in carrying out the surgical procedure. When using the instrument the surgeon manipulates the stomach tissue with graspers and/or applies suction to decompress the stomach and visualize where the sizing tube is located, like described above with respect to the other embodiments of the invention. In addition to this clinically established approach to visualization, the instrument 520 further aids visualization by near infrared transillumination. Through the added NIR transillumination, the location of the sizing tube within stomach is clearly visualized without the need to manipulate the tissue with graspers or to decompress it by applying suction. This effect is applicable under any laparoscope that can detect NIR light. For example, Intuitive da Vinci robotic camera system includes a NIR-sensitive mode (Firefly), where the RGB colors are assigned into greyscale, and the NIR wavelength is represented as green color.

In accordance with one preferred exemplary embodiment of the instrument 420, and as will be described in more detail later, the electrical power source 530 is a battery pack composed of two non-rechargeable AAA alkaline batteries B1 and B2 which are connected in series to produce an open circuit voltage of 3.3 VDC. The power source actuator 532 is in the form of a battery insulator pull tab that comprises a strip of an electrical insulating material which is interposed between one of the poles of the battery pack to isolate the batteries B1 and B2 from the elongated light source 528. Thus, the pull tab 532 can be thought of as a single use OFF/ON switch, which when the tab is in place the switch is in its Off state to prevent the batteries from applying electrical power to the elongated light source 528. Removal of the pull tab by the user of the instrument effectively "closes" the switch to apply the electrical power from the batteries B1 and B2 to the elongated light source 528 via the electrically conductive cable 534. That action energizes the elongated light source. Once energized the elongated light source will produce light for at least one hour. The cable carrying the electrical power to the elongated light source is preferably composed of a pair of 30 AWG electrical conductors C1 and C2. In this exemplary embodiment conductor C1, which is connected to the negative terminal of the battery pack, is a tinned copper conductor, whereas conductor C2, which is connected to the positive terminal of the battery pack, is bare copper.

Figure 20:
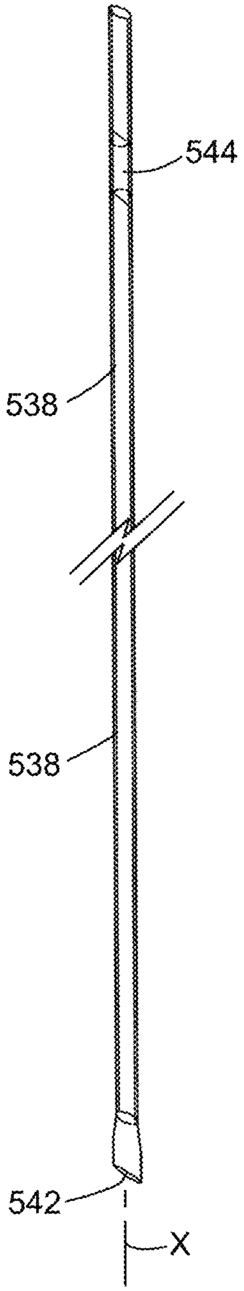
FIG. 20 is an enlarged isometric view of a portion of the instrument, namely, an encasement sleeve for holding a flexible circuit including plural spaced apart light emitting diodes which forms a portion of the illumination source of the subject invention to protect the flexible circuit from gastric fluids.
Figure 21:
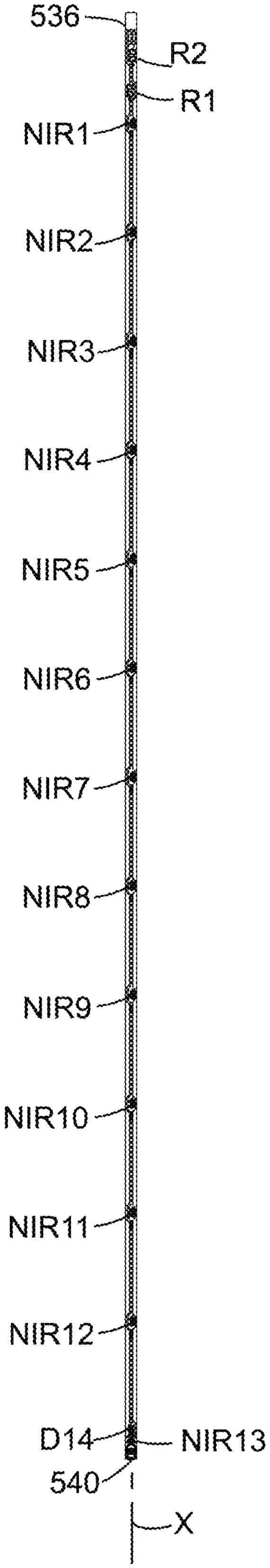
FIG. 21 is an enlarged isometric view of the flexible circuit that is held within the encasement sleeve of FIG. 20.

As best seen in FIGS. 19 and 21 the elongated light source 428 basically comprises an elongated strip 536 in the form of a flexible circuit having a longitudinal axis X. The flexible circuit strip is disposed and sealed within the encasement sleeve 538 (FIGS. 16 and 20) to protect the components of the flexible circuit from gastric fluids when the sizing tube is disposed within the patient's stomach. The details of the construction of the flexible circuit 536 will be described later. Suffice it for now to state that flexible circuit includes a plurality of light-emitting diodes, two resistors, and various electrical conductor segments connecting those components to one another. The light emitting diodes are arrayed sequentially at equidistant spacing on the strip and are configured to emit light at two wavelengths, e.g., as visible red light and as near infrared (NIR) light. The visible red light is provided by a single LED which emits visible red light in the range of approximately 610 nm to 660 nm and with a peak intensity (λpeak) at approximately 645 nm. The near-infra red light is provided by an array of NIR LEDs which emit near infrared light in the range of approximately 780 nm to 880 nm with a peak intensity (λpeak) at approximately 850 nm. This emission spectrum overlaps with emission spectrum of Indocyanine Green (ICG), a fluorescent dye commonly administered intravenously during gastric and bariatric surgery. Modern laparoscopes sensitive to NIR light are sensitive to ICG emission and thus are able to detect the NIR wavelengths emitted from the NIR light emitters.

The emitted light can be observed directly by user, while still outside of the body, or indirectly by a NIR-sensitive laparoscope during surgery. As will be described in more detail shortly, the single visible red LED light is located near the distal tip of the device. The red light produced by the red LED is readily detected by both human eye and by cameras as a red color. The purpose of the visible red light is to confirm to the user that removal of the battery insulator has in fact energized the light emitting array. The near-infra red light serves to transilluminate tissue making up the wall of the stomach to assist with visualizing the location of sizing tube inside of the GI tract.

The NIR light emitting diodes are configured in a 300 mm long array with 25 mm spacing between them. Although patient anatomy varies, the array length can span approximately the full length of stomach from the pylorus to lower esophageal sphincter. The emitted wavelength of the NIR light emitting diodes ranges from approximately 780 nm to approximately 880 nm with a peak intensity at approximately 850 nm.

Figure 23:
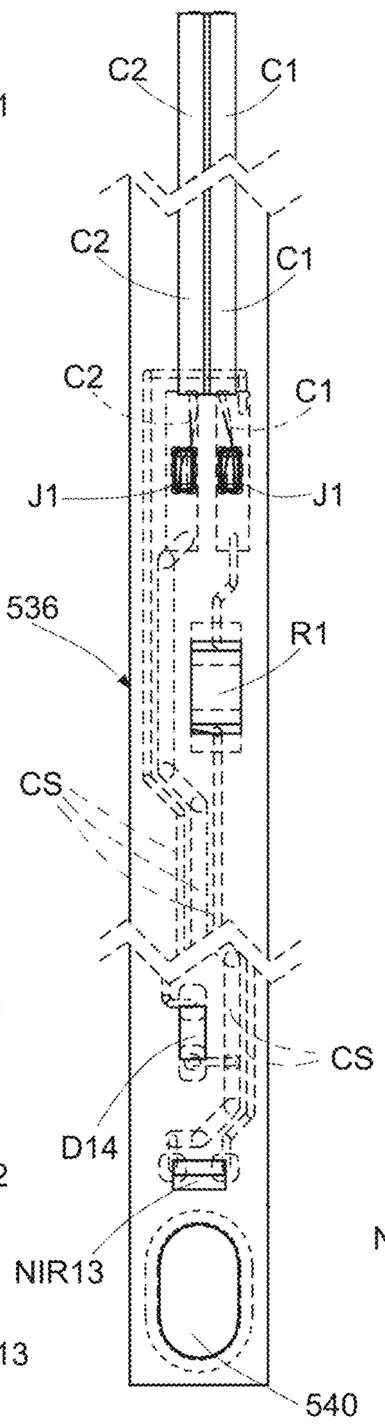
FIG. 23 is a greatly enlarged plan view of the distal end of the assembly shown in FIG. 22.
Figure 24:
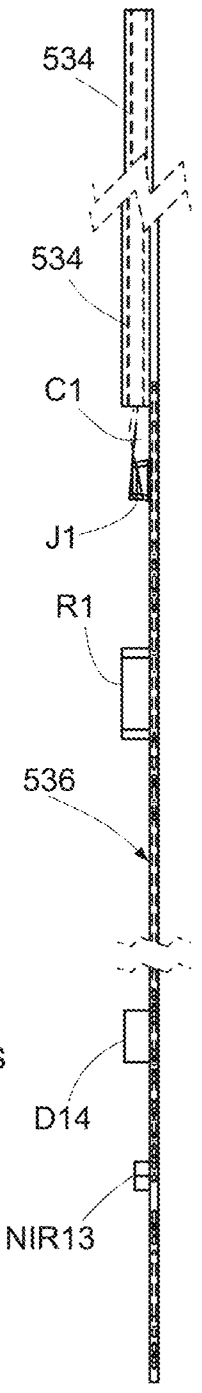
FIG. 24 is a greatly enlarged side elevation view of the distal end of the assembly shown in FIG. 22.
Figure 25:
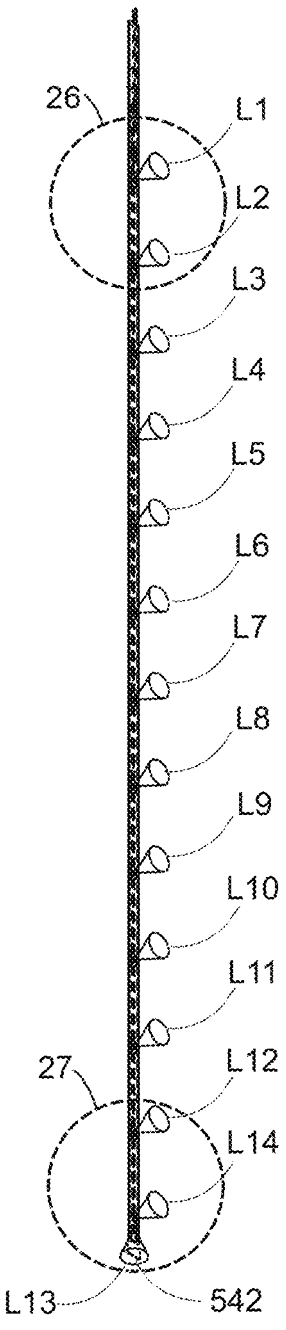
FIG. 25 is an illustration showing the light emitted from the light emitting diodes of the flexible circuit shown in FIGS. 22-24.
Figure 27:
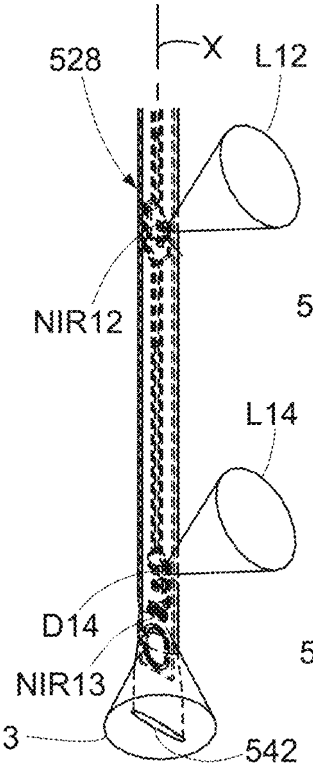
FIG. 27 is an enlarged illustration of the portion of the illustration shown within the broken circle designated by the reference number 27 in FIG. 25.

As best seen in FIGS. 19 and 21 the flexible circuit 536 is composed of a resistor R1, a resistor R2, an array of parallel connected near infrared light emitting diodes NIR1, NIR2, NIR3, NIR4, NIR5, NIR6, NIR7, NIR8, NIR9, NIR10, NIR11, NIR12, and NIR 13, and a visible red light emitting diode D14. As mentioned earlier the flexible circuit 536 is located within an encasement sleeve 538 like shown in FIGS. 16 and 20. The encasement sleeve is preferably a flexible tube formed of medical grade polyurethane which is clear or otherwise transparent so that the light emitted by the light emitting diodes can freely pass therethrough. The flexible circuit 536 is disposed in the encasement sleeve by introducing the distal end of the flexible circuit into the proximal end of the encasement sleeve, which is open at that time. As best seen in FIG. 23 a hole or window 540 is located immediately adjacent the distal end of the flexible circuit. That hole provides a means for grasping the distal end of the flexible circuit to pulling it into the encasement sleeve until its distal end is located adjacent the open distal end of the encasement sleeve. Once in that position the open distal end of the encasement sleeve is permanent closed by squeezing the distal end so that it is flat and heat sealing the abutting surfaces of the flattened distal end of the encasement sleeve together to form a fluid-tight joint 542 (FIGS. 20 and 27). The conductors C1 and C2 exit from the proximal end of the flexible circuit strip and hence pass out the open proximal end of the encasement sleeve. As shown in FIG. 20 a sealant, such as a UV curable silicone, is introduced into the interior of encasement sleeve from the open proximal end to form a sealed joint 544 through which the conductors C1 and C2 of the cable extend. Accordingly, the flexible circuit is completely enclosed and isolated in the sleeve between the joints 542 and 544 and so that gastric fluids cannot gain access to the flexible circuit when the sizing tube is located within the patient's stomach.

Figure 26:
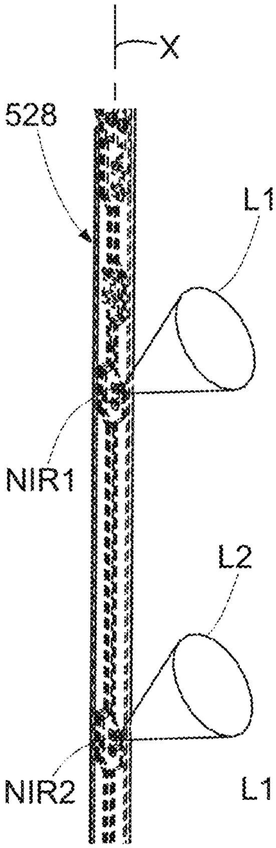
FIG. 26 is an enlarged illustration of the portion of the illustration shown within the broken circle designated by the reference number 26 in FIG. 25.

The array of parallel connected NIR light emitting diodes NIR1-NIR12 are physically oriented so that the NIR light produced from each diode projects perpendicularly upward from the longitudinal axis X and through the sidewall of the encasement sleeve. This feature is illustrated in FIG. 26, wherein the NIR light produced by the NIR1 and NIR2 diodes are graphically illustrated as cones of light designated by the reference number L1 and L2, respectively. The lights L1 and L2 each project upward from the plane of the flexible circuit strip and perpendicular to its longitudinal axis X. In FIG. 27 the NIR light produced by the NIR12 diode is graphically illustrated as a cone of light designated by the reference number L12 and which also projects upward from the plane of the flexible circuit strip perpendicular to its longitudinal axis X. The NIR light emitting diode NIR13 is located at the distal end of the flexible circuit and is oriented sideways so that the NIR light produced thereby, which is illustrated by the cone of light L13 in FIG. 27 as projects distally from the distal end of the flexible circuit parallel to the longitudinal axis X and out the distal end 440 of the encasement sleeve 538 and through the rounded atraumatic tip 28 of the sizing tube.

The NIR light produced by the diodes NIR1-NIR12 is preferably in the range of approximately 810 nm to approximately 880 nm, with a peak (λpeak) at approximately 850 nm nm. The NIR light produced by the diode NIR13 is preferably in the range of approximately 780 nm to approximately 880 nm, with a peak (λpeak) at approximately 850 nm.

The visible red light emitting diode D14 is physically located between the NIR13 light emitting diode and the NIR12 light emitting diode and is oriented so that the visible red light produced thereby, which is illustrated by the cone of light L14 in FIG. 27, projects perpendicularly upward from the plane of the flexible strip and perpendicular to its longitudinal axis X and through the sidewall of the encasement sleeve.

The NIR light emitting diodes NIR1-NIR13 are configured to produce near infrared light as described above when energized by the batteries B1 and B2, i.e., when the pull tab 532 is removed. The near infrared light produced can be sensed by a conventional laparoscope camera like those used during the bariatric procedure as described above. Thus, when the illuminated sizing tube of the instrument 500 is located within the patient's stomach and the NIR light emitting diodes energized the NIR light produced will pass through the wall of the stomach to be picked up by the laparoscope camera, thereby transilluminating the patient's stomach and providing a visual indication of the location of the sizing tube with respect to the patient's stomach. As should be appreciated by those skilled in the art the transilluminated portion of the patient's stomach will be located closely adjacent the visually perceptible sealing line created by the application of suction to the patient's stomach as described above with respect to the embodiments of FIGS. 1-13B. That transillumination will provide additional visualization for the surgeon when the sizing tube is inside the GI tract, e.g., when performing the resection patient's stomach along the visually perceptible line.

The visible red light produced by D14 serves to provide the user of the device, e.g., the clinician, with a means to determine if the elongated light source 528 is operative before the device is introduced into the stomach of the patient. To that end, before introduction into the patient a user of the device can test the device by removing the insulator strip 532, thereby causing electrical power from the batteries B1 and B2 to be applied to the LEDs of the elongated light source 528. That action should result in the energization of the diode D14 and the production of visible red light therefrom. In such a case, if the user of the device sees red light emanating from the diode D14 he/she will know that the illumination light source has been energized. Thus, the NIR light emitting diodes NIR1-NIR13 should be producing the NIR light, even though such light is of a wavelength that cannot be seen by the user's eyes (but can be seen by a laparoscopic camera).

Turning now to FIG. 19 the electrical connection of the components making up the electrical subsystem 524 will now be discussed. Thus, as can be seen, one side of the resistor R1 is connected to a solder joint J1, which is connected to the distal end of the cable conductor C1. The opposite side of the resistor R1 is connected to the cathodes of the NIR light emitting diodes NIR1-NIR13. One side of the resistor R2 is connected to the solder joint J1. The opposite side of the resistor R2 is connected to the cathode of the visible red light emitting diode D14. The anode of the visible red light emitting diode D14 is connected to the anodes of the NIR light emitting diodes NIR1-NIR13 and to a solder joint J2. The solder joint J2 is connected to the distal end of the cable conductor C2. The proximal end of the cable conductor C1 is connected to the negative terminal of the battery pack 530 by solder joint J3. The proximal end of the cable conductor C2 is connected to the positive terminal of the battery pack 530 by solder joint J4. As mentioned earlier the battery pack is preferably composed of two alkaline AAA batteries B1 and B2. The resistor R1 reduces the voltage applied from the batteries B1 and B2 to the light emitting diodes NIR1-NIR13 to their nominal operating voltage of approximately 1.6 VDC to enable those diodes to produce NIR light of a sufficient intensity while protecting those diodes from overvoltage which could damage them. The resistor R2 reduces the voltage applied from the batteries Bland B2 to the visible red light emitting diode D14 to its nominal operating voltage of approximately 2.1 VDC to enable those diodes to produce NIR light of a sufficient intensity while protecting that diode from overvoltage which could damage it.

A portion of the layout of the components of the flexible circuit 536, e.g., NIR1-NIR13, D14, R1, R2 and the electrical conductor sections CS which connect those components, are shown in FIG. 23 and that layout is produced by using a Gerber file layout.

Figure 29:
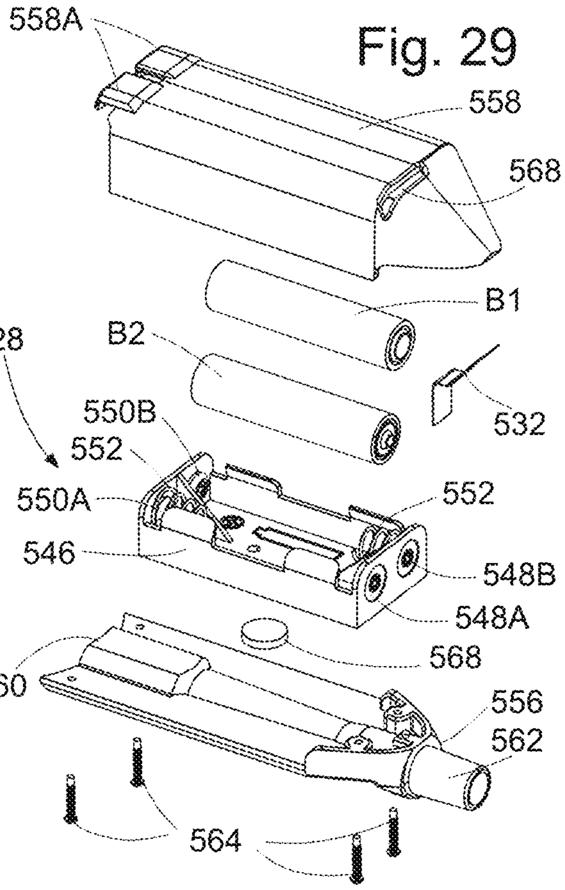
FIG. 29 is an enlarged exploded isometric view of a portion of the components making up the electrical power source and its housing of the instrument of FIG. 14.
Figure 28:
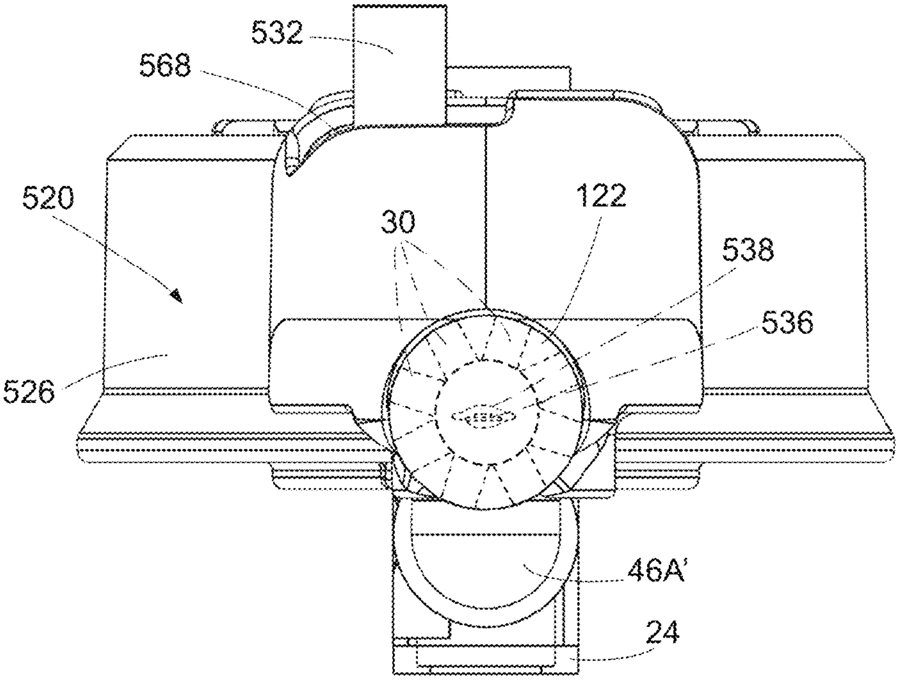
FIG. 28 is a greatly enlarged distal end view taken along line 28-28 of FIG. 14.
Figure 30:
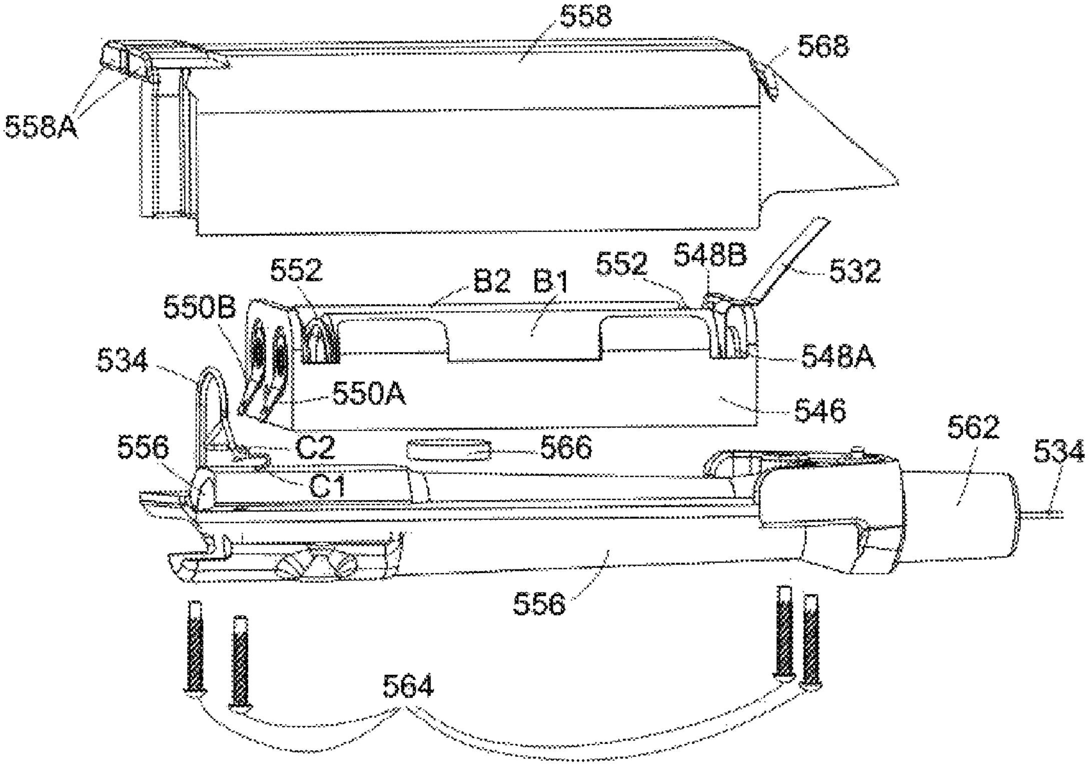
FIG. 30 is another enlarged exploded isometric view of the electrical power source shown in FIG. 29.

Turning now to FIGS. 29 and 30 the details of the battery pack 530 and its associated components will now be described. The batteries B1 and B2 making up the battery pack are connected in series and held in a conventional battery case or receptacle 546, which in turn is mounted and enclosed within a housing to be described later. The battery case includes a pair of electrical contacts 548A and 548B located at the distal end of the case 546 and which are electrically connected. The contact 548A is configured to be engaged by the positive terminal of the battery B1. The contact 548B is configured to be engaged by the negative terminal of the battery B2. The opposite, i.e., proximal, end of the battery case includes another pair of electrical contacts 550A and 550B. A helical compression spring 552 is interposed between the negative pole of the battery B1 and the electrical contact 550A so that the negative pole of that battery is in electrical continuity with that contact. Another helical compression spring 552 is interposed between the positive pole of the battery B2 and the electrical contact 550B so that the positive pole of that battery is in electrical continuity with that contact. The proximal end of the conductor C1 is connected to the electrical contact 550A by solder joint J3. The proximal end of the conductor C2 is connected to the electrical contact 550B by solder joint J4. Thus, the springs 552 bias the batteries B1 and B2 in series and into electric continuity with electrical contacts forming the positive and negative poles of the battery pack 532.

The battery case with its batteries B1 and B2 is mounted within a housing 454. The housing 554 is composed of a base 556 and a cover 558. The base includes a socket 560 configured for receipt of the line suction port 26A' of the suction controller 526. That action secures the housing 454 to the suction controller 426. A passageway (not shown) extends from the socket in the base 556 of the housing to a tubular port 562 at the distal end of the base 556. The tubular port 562 is configured to receive the open proximal end of the sizing tube 122 to provide the regulated suction into the proximal end of the sizing tube and down its passageway 22A to the array of apertures 30. The cover 558 of the housing 554 is a hollow member which is secured to the base 556 via four nail screws 564 extending through aligned holes in the base and cover. The cover includes a pair of tabs 558A projecting proximally at the top of the cover 558. The tabs are configured to engage contiguous portions of the top surface of the top wall 60' of the suction regulator 526 to assist in the securement of the housing 554 to the suction controller. When so secured the battery pack is enclosed within the interior of the housing. A disk 566 formed of silicone foam with an adhesive backing is disposed between the bottom surface of the battery case 546 and the base of the housing to act as vibration insulator to prevent the battery case from rattling within the housing 554.

The cover 558 includes a slot 568 through which a portion of the power source actuator or pull tab 532 extends so that the portion of the pull tab extending out of the housing can be readily grasped by a user and pulled through a slot so that its interior end is no longer interposed between the positive (+) pole of battery B1 and the electrical contact 548A. Accordingly, when it is desired to energize the illumination circuitry of the instrument 520 all that is required is for the user to grasp the exposed end of the pull tab 532 that extends out of the slot 568 to pull it outward, so that electrical power is delivered to the light emitting diodes of the instrument to cause them to illuminate.

Figure 22:
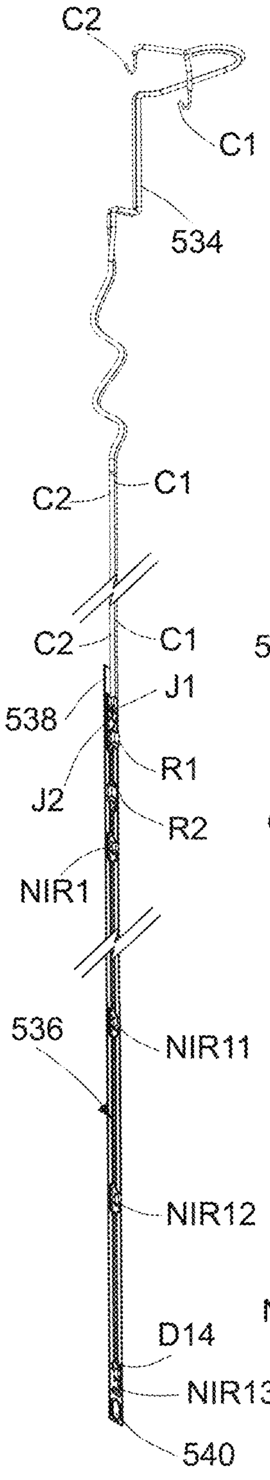
FIG. 22 is an isometric view of a portion of the illumination source, namely, the assembly of the flexible circuit and its associated electrically conductive cable, with the flexible circuit being shown located within the encasement sleeve.

As mentioned earlier the proximal end portion of the conductors C1 and C2 of the cable 434 are connected via solder joints J3 and J4 to respective the respective negative and positive terminals of the battery pack 530. As best seen in FIG. 22 portions of the conductors C1 and C2 adjacent the proximal ends of the cable 534 are bent into a somewhat sinusoidal or wavy shape to be able to flex to accommodate the flexing of the flexible circuit 536 and the associated cables as the sizing tube is bent into engagement with the lesser curvature of the patient's stomach when in use.

Turning now to FIGS. 31-41 the details of the construction of the suction controller or regulator 526 will now be described. That suction controller/regulator is constructed in accordance with the teachings of U.S. Pat. No. 11,389,318, which is assigned to the same assignee as the subject invention and whose disclosure is incorporated by reference herein. In particular, the suction controller 426 of this invention is constructed similarly to the suction regulator of U.S. Pat. No. 11,389,318. To that end, the details of the construction of the suction controller 526 will be described hereinafter, with the component parts thereof as shown in FIGS. 31-41 and as described below being identified by corresponding reference numbers to those of the suction regulator 26 of U.S. Pat. No. 11,389,318 but including a prime symbol. As such, the suction controller 526 basically comprises a label 34', a lid or cover 36', a flexible diaphragm 38', a piston 40', a sealing disk 42', a helical compression spring 44', and a housing body 46'. The lid or cover 36' and the housing body 46' are configured to be connected, as will be described later, to form a hollow housing assembly for housing the other components making up the controller. The housing body 46' and the cover 36' are each formed of a rigid plastic, such as ABS.

As best seen in FIGS. 32, 39, 40 and 41, the housing body 46' includes a circular annular sidewall 48' projecting upward from a bottom wall 50'. The circular sidewall extends about a central axis X of the suction controller. A tubular extension 46A' extends generally parallel to the undersurface of the bottom wall 50'. The tubular extension 46A' forms line suction port 26A' and includes a passageway 52' extending through it. The passageway 52' includes a linear section 52A' extending radially from the axis X and whose outer or free end is open. The opposite end of the linear passageway section 52' terminates in an axially directed passageway section 52B centered about the axis X and terminates at the bottom wall 50'. The upper end of the passageway section 52B' is open at 52C', with the portion of the bottom wall 50' contiguous with the opening 52C' forming a beveled or conical surface valve seat 54'. The opening 52C' is in fluid communication with a lower chamber 56' within the interior of the suction controller. The lower chamber 56' is partially defined by the inner surface of the annular sidewall 48' and the diaphragm 38'. Another tubular extension 46B' projects radially outward from the annular sidewall 48'. That tubular extension forms the heretofore identified line suction port 26B' and includes a passageway 58' extending through it. The passageway 58' extends radially from the central axis X and parallel to the longitudinal axis of the passageway section 52A'. The outer or free end of the passageway 58' is open. The inner end of the passageway 58' terminates at the sidewall 48' and is open and in fluid communication with the lower chamber 56' of the suction controller.

The lid or cover 36' is a generally cup-shaped member having a top wall 60' and a circular annular sidewall 62'. The sidewall includes a pair of diametrically opposed notches 64' immediately adjacent the lower edge of the sidewall. The notches are configured to receive respective diametrically opposed projecting tabs 66' of the housing body 46' to secure the lid or cover 36' to the housing body 46' and thus complete the housing assembly. The sidewall 62' of the lid or cover also includes an arcuate recess 68' (FIGS. 31 and 33) in the lower edge of the sidewall located midway between the notches 64'. The recess 68' serves to receive the tubular extension 46B' when the lid or cover is secured to the housing body.

The piston 40 is best seen in FIGS. 32, 35, 36, and 37 and basically comprises a unitary body formed of a rigid plastic, such as ABS. The body includes a central hub 70' whose top end terminates in a circular flange 72'. The top surface of the flange is planar but includes a circular recess 74' in the center thereof and extending into the hub 70'. A plurality of ribs 76' extend outward radially from the hub and serve to reinforce the flange and center the spring 44' about the central axis X. The bottom surface of the hub 70' includes a recess 78' for receipt of the sealing disk 42'. The disk 42' is fixedly secured in the recess 78' on the underside of the hub serves as a valve member to engage the valve seat 54' in the lower chamber 56' when excess suction is applied. The sealing disk 42' is formed of any suitable material, e.g., silicone rubber.

The diaphragm 38' is a rolling diaphragm formed of any resilient flexible material, e.g., Nitrile. The diaphragm includes a generally planar circular central portion 80' and a folded generally V-shaped or U-shaped edge portion 82' surrounding the central portion and terminating in a flanged generally planar thickened periphery 84'. When fabricated the diaphragm is a molded component which is somewhat flat, but whose peripheral edge portion contiguous with the planar thickened periphery is everted (turned inside out) to assume the shape shown in FIGS. 32, 34, and 40 for use in the suction controller. A small opening or hole 86' is located in the center of the central portion 80'. The central portion 80' is disposed on the planar top surface of the piston 40', with the thickened periphery 84' of the diaphragm disposed on an annular ledge 88' at the upper end of the sidewall 48' of the housing body 46' between that ledge and the undersurface of the lid or cover 36'. With the lid or cover secured to the housing base 46' the thickened periphery 84' of the diaphragm is tightly sandwiched between the ledge and the inner surface of the lid or cover. This arrangement divides the interior of the suction controller into two chambers, namely, the lower chamber 56' and an upper chamber 90'. The upper chamber is formed between the inner surface of the cover or lid and the upper surface of the diaphragm. The lower chamber 56' is formed between the inner surface of the sidewall 48' of the housing body 46', and the undersurface of the portion of the diaphragm located adjacent its periphery and a portion of the undersurface of the piston.

Figure 31:
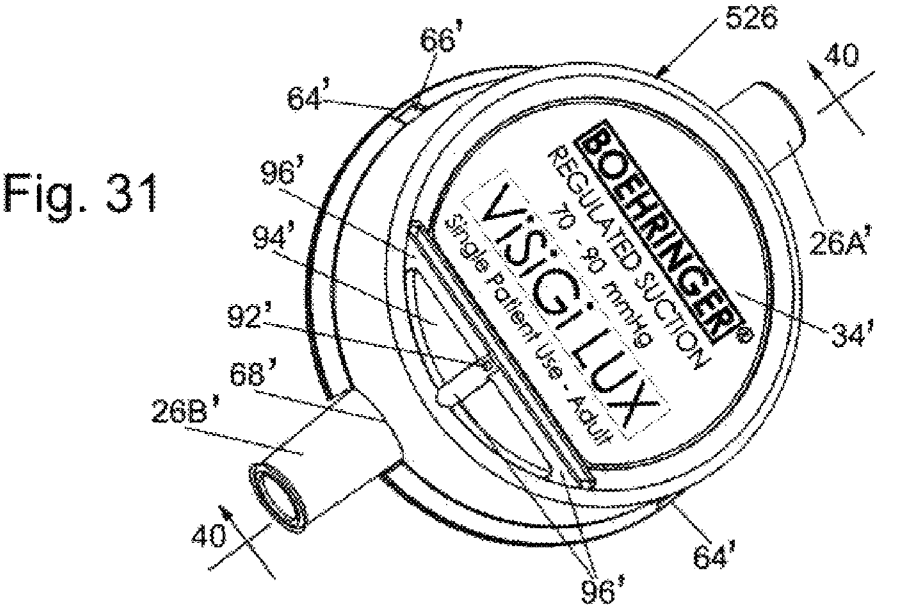
FIG. 31 is an enlarged isometric view of one of the components, i.e., the suction regulator, forming a portion of the system of FIG. 14.
Figure 32:
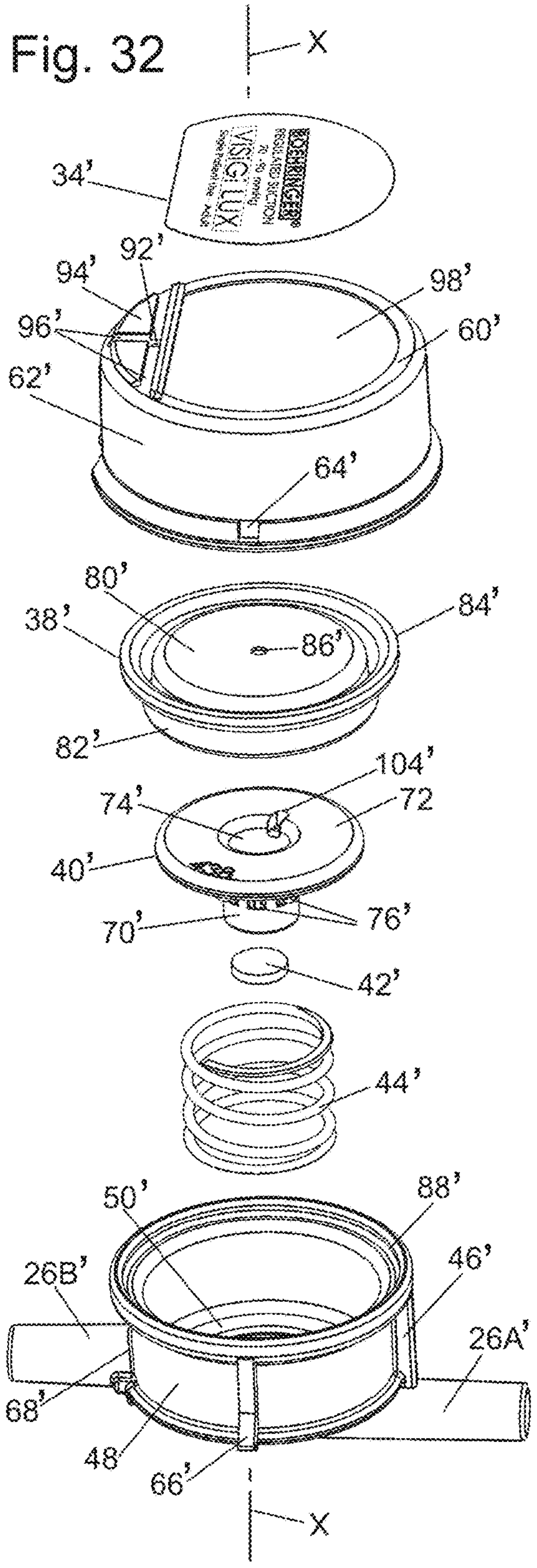
FIG. 32 is an exploded isometric view of the components making up the suction regulator shown in FIG. 31.
Figure 33:
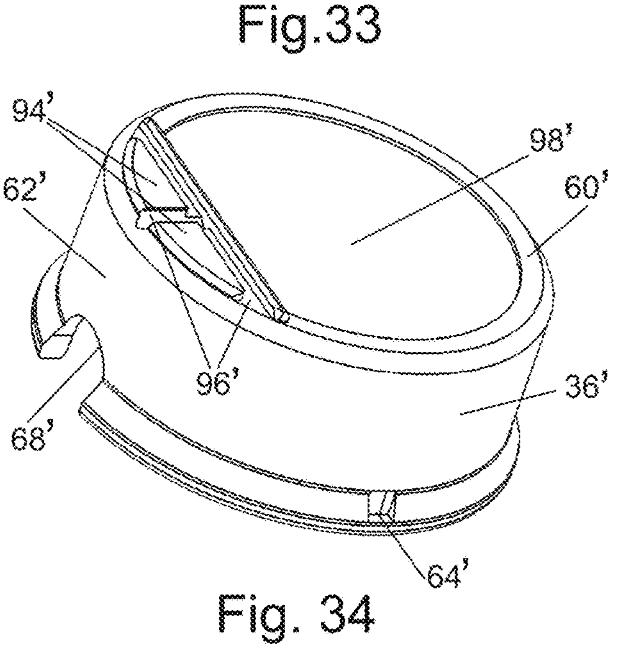
FIG. 33 is an enlarged isometric view of one of the components, i.e., a cap or lid, of the suction regulator shown in FIG. 31.
Figure 34:
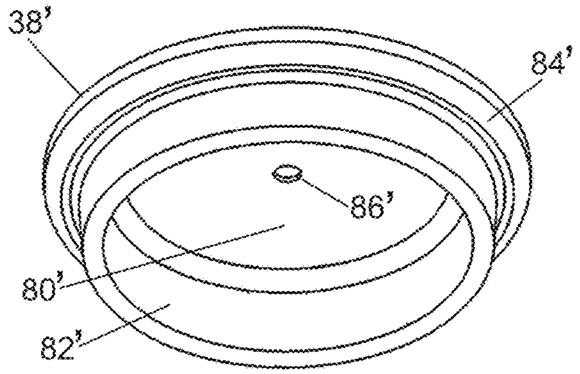
FIG. 34 is an enlarged isometric view of another of the components, i.e., a diaphragm, of the suction regulator shown in FIG. 31.
Figure 35:
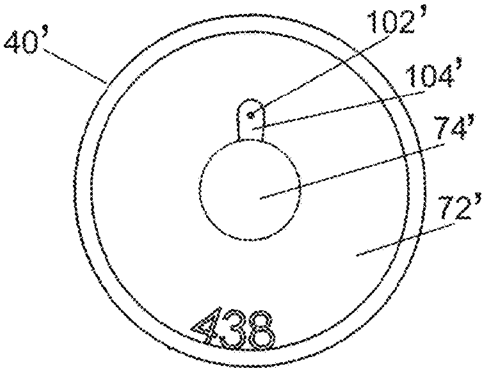
FIG. 35 is an enlarged top plan view of another of the components, i.e., a piston, of the suction regulator shown in FIG. 31.
Figure 40:
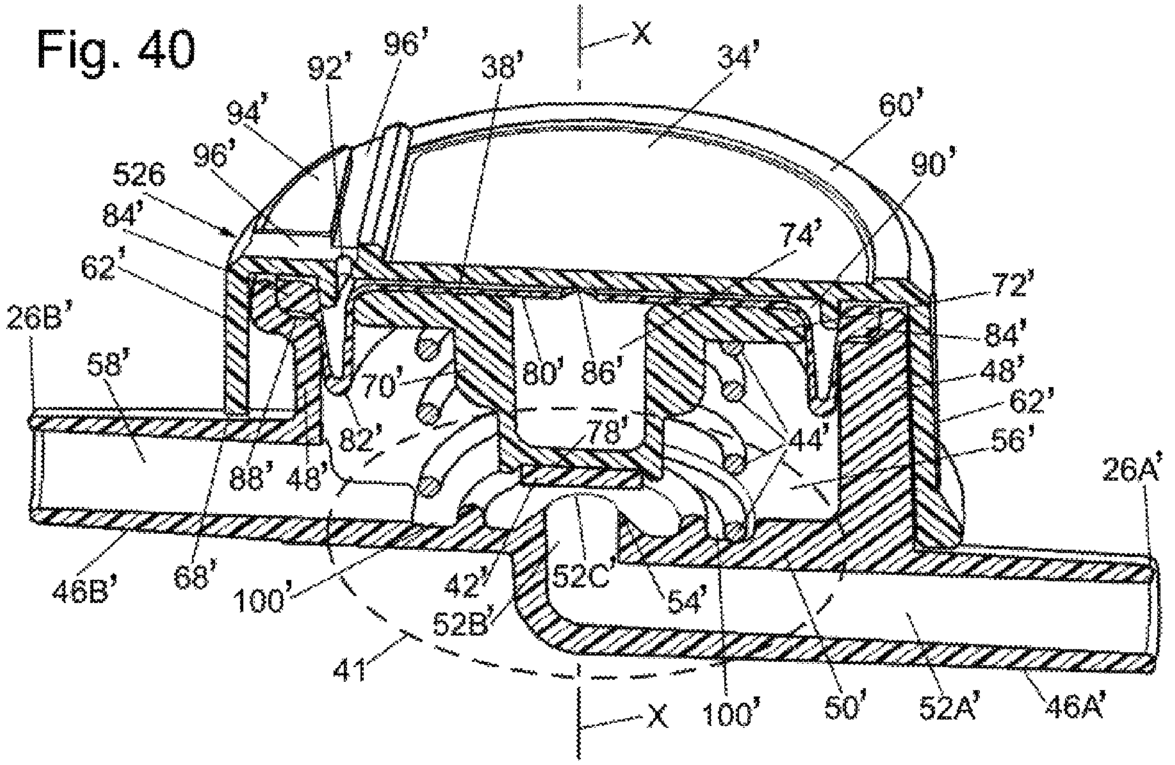
FIG. 40 is an enlarged sectional view taken along line 11-11 of FIG. 31.

The cover or lid includes a small opening or vent to the ambient atmosphere which will be referred to as the atmospheric reference port 92' (FIGS. 31 and 40). The atmospheric reference port ensures that the upper chamber 90' will be at the pressure of the ambient atmosphere. In particular, the port 92' extends through the thickness of the cover and is in fluid communication with the interior of upper chamber 90' to maintain that chamber at atmospheric pressure. Inasmuch as the atmospheric reference port 92' is located in the top surface of the cover, it is susceptible to being blocked or covered by a sticker, some other object or even the finger of a user. To prevent such an occurrence the lid or cover is shaped to prevent blockage of the port 92'. In particular, the lid or cover includes a thickened portion 94' located adjacent the port 92' with an elongated shallow tripartite or T-shaped recess or slot 96' extending into the thickened portion. The outer or top end of the atmospheric reference port 92' is located at the bottom of the slot 96' at the intersection of the slot's various three sections and is in fluid communication with each of those sections. The outer end of each of the slot sections is open. Thus, if something should be on the top surface of the thickened portion 94' of the lid or cover disposed over the atmospheric reference port 92' air can still enter that port via any open end of the T-shaped slot 96'.

The label 34', which is configured to bear indicia or information regarding the suction controller, e.g., text and graphics, is fixedly secured within a very shallow recess 98' (FIG. 33) in the top surface of the lid or cover adjacent the thickened portion 94' so its presence does not block the T-shaped slot 96'.

Figure 41:
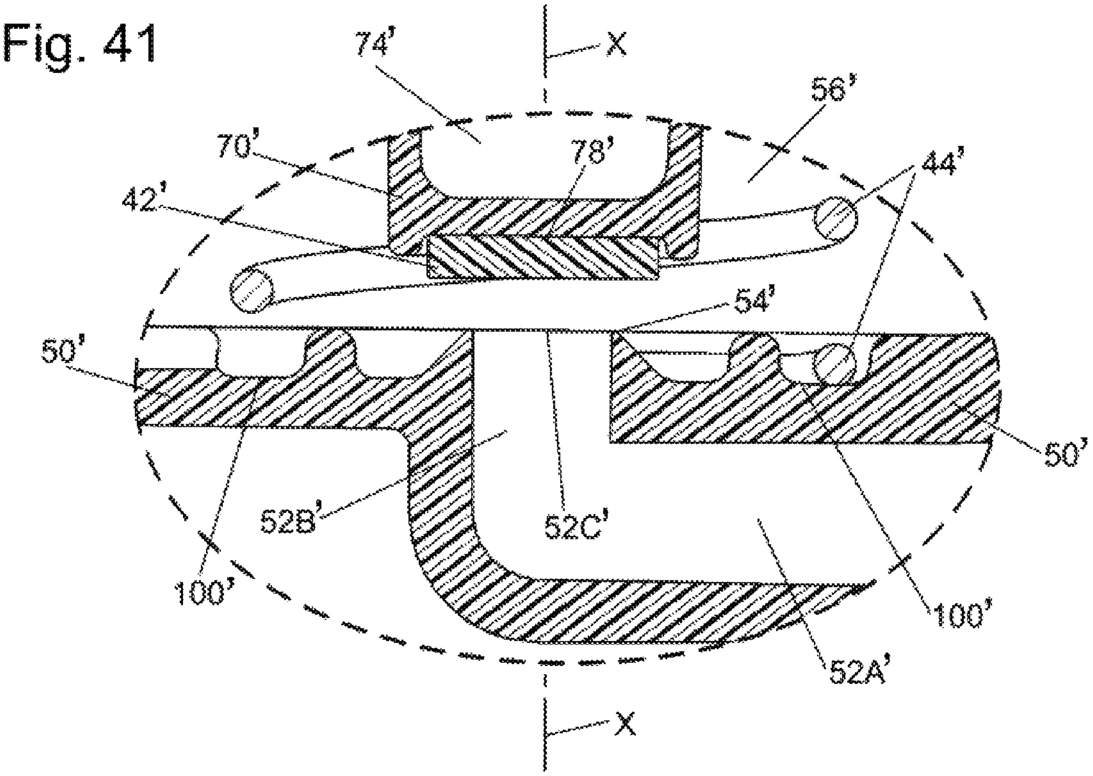
FIG. 41 is an enlarged sectional elevation view of the portion of the suction regulator shown within the broken oval designated by the reference number 41 in FIG. 40.

The spring 44' is a helical compression spring formed of any suitable material, e.g., stainless steel. As best seen in FIGS. 40 and 41, the spring is located within the lower chamber 56', with the upper end of the spring in engagement with the undersurface of the flanged portion 72' of the piston and surrounding a piston's central hub 70' and with the lower end of the spring located within an annular recess 100' in the bottom wall 50' of the housing body. The spring is under compression to bias the piston and diaphragm upward.

The suction controller 426 regulates the level of suction to a desired operating value as described above and provides the regulated suction to the passageway 22A. To that end, the controller is configured to limit the amount of suction applied to the external catheter to that desired value even if a level of suction greater than that predetermined value is applied to the suction controller from the suction source (particularly if the suction source is at a much higher level, which will typically be the case if the suction source is the hospital's suction line). The predetermined or desired suction value (hereinafter referred to has the "controller's set-point" or "regulated set-point value") is fixed and is factory-established by the spring 44' and the dimensions of the housing body 46', the cover or lid 36', the piston 40', the sealing disk 42', and the stiffness of the diaphragm 38'. In this regard the pressure within the upper chamber 90' will be equal to atmospheric pressure by virtue of the communication of that chamber with the ambient atmosphere via the atmospheric reference port 92'. With suction applied, the pressure within the lower chamber 56' will be lower than the atmospheric pressure within the upper chamber 90'. The differential pressure between the chambers 90' and 56' will force the diaphragm 38' and the piston 40' downward toward the valve seat 54'. The spring 44', however, will impart a counter force on the piston and diaphragm that opposes the differential pressure force forcing the piston downward such that the level of suction appearing at the regulated suction port 46B' is the desired operating value.

If the suction applied via line suction port 26A' is greater that the predetermined value or level the piston 40' and diaphragm 38' will move such that the sealing disk 42' on the bottom of the piston's hub 70' comes into engagement with the valve seat 54' thereby isolating the lower chamber 56' from the suction appearing on the line suction port 26A'. This action thereby limits the level of suction in lower chamber and ultimately to the central passageway 22A of the sizing tube 122 and from there to the communicating apertures 30 to the predetermined operating value. If, however, the suction applied via line suction port is less than the predetermined operating level or value the piston and diaphragm will only move part of the way downward. As such the level of suction applied to the line suction port 26A' will equal that in the regulated suction port 26B' and that applied to the sizing tube 122.

It should be pointed out at this juncture that the suction controller is also configured to prevent the sealing disk 42' on the bottom of the piston from becoming stuck for an extended period of time on the valve seat 54' in the event of what will be referred to hereinafter as an "over-travel situation". In this regard, it has been determined that if the suction controller is operated in a manner such that a high level of suction is applied very rapidly, the piston may experience an over-travel wherein it moves downward very quickly such that the scaling disk 42' on the underside of the piston becomes stuck on the valve seat 54'. Under this condition the sizing tube would have a higher level of vacuum (suction) than the suction controller was set to provide. To prevent such an occurrence, the suction controller includes two "bleed holes". One bleed hole is the heretofore identified small hole 86' located in the center of the diaphragm 38'. The second bleed hole 102' is located in the piston 40'.

As best seen in FIGS. 32, 35, 36, and 37 the cylindrical cavity 74' in the piston contiguous with the planar top surface of the flanged portion 72' includes a radially extending recess. The bleed hole 102' is located in that recess and extends through the flanged portion of the piston to the underside of the flanged portion as best seen in FIG. 36. Since the bleed hole 86' in the diaphragm is located in the center thereof, i.e., on the central axis X, it will overlie and be in fluid communication with the cylindrical cavity 74' in the piston. The recess 104' is in fluid communication with the cylindrical cavity 74'. Thus, the bleed hole 102' in the piston will be in fluid communication with the bleed hole 86' in the diaphragm. Since the bleed hole 86' in the diaphragm is in communication with the upper chamber 90', that chamber will be in fluid communication with the lower chamber 56' via the communicating bleed holes 86' and 102'. Hence, if the sealing disk 42' on the bottom of the piston should become stuck on the valve seat 54', air which enters into the upper chamber 90' via the atmospheric reference port 92' can then pass through the bleed hole 86' into the cylindrical cavity 74', and from there through recess 104' into the bleed hole 102', from whence it will enter into the lower chamber 56'. The ingress of air into the lower chamber will decrease the vacuum within that chamber, thus enabling the spring 44' to move the piston 40' upward so that the sealing disk 42' is off of the valve seat 54'.

In accordance with the exemplary preferred embodiment of the suction controller 426, the inner diameter of the lower chamber 56' is approximately 1.5 inch. The inner diameter of the upper chamber is approximately 1.5 inch. The spring is configured to naturally apply a bias force of approximately 1.0 pound. The inner diameter of the passageway 54' is approximately 0.25 inch. The inner diameter of the passageway 58' is approximately 0.25 inch. The opening 52C' located within the bounds of the valve seat 54' is approximately 0.22 inch. The atmospheric reference port 92' is approximately 0.035 inch in diameter. The bleed hole 102' is approximately 0.016 inch in diameter. The bleed hole 86' is approximately 0.062 inch in diameter. In accordance with one commercial embodiment of the instrument 420, the sizing tube 122 is approximately 104 cm long. It can come in three outside diameters, namely, 40 French, 36 French, and 32 French. As is known, 3 French=1 mm diameter. The apertures or holes 30 are disposed in an array that extend to a distance of approximately 13 cm from the distal end or tip 28.

Usage of the instrument 520 will typically be accomplished in accordance with the Instructions For Use (like shown in FIG. 42) in the sequence described below and in accordance with Instructions For Use (IFU) shown in FIG. 42. In particular, the instrument 520, which is identified in the IFU under the trademark VISIGI® LUX, is used as an orogastric tube during bariatric and gastric surgery. To that end, the instrument is provided non-sterile in a clear packaging and when ready for use is removed from the packaging. The user can then remove the battery insulator pull tab 532, whereupon the visible red light at the distal end of the sizing tube as produced by the LED D14 lights up to indicate that the instrument is energized. The user then ensures that the suction (slide) valve 24 is set to its open state. The user then applies surgical lubricant generously onto the tip 28 of the sizing tube before inserting it into patient. If the procedure to be carried out with the instrument will be accomplished with a laparoscopic or robotic camera with NIR mode, the user will select the appropriate camera mode to enable NIR-assisted visualization of the instrument. The instrument is then advanced into the patient's stomach under direct visualization by surgeon's direction or is inserted the same way as a conventional orogastric (OG) tube. The user will stop insertion once gastric contents are visible. The sizing tube of the instrument includes length markings at 30, 40, and 50 cm there along. The user should not pass the third marking (50 cm) without laparoscopic visualization. For sizing applications the user will position the instrument within the stomach as desired and connect the instrument to a source of suction. To remove fluid, enable irrigation, or to apply suction, the slide valve 24 is moved to its open position. When moving or removing the instrument the application of suction to the instrument is stopped. The instrument is vented by placing the slide valve in its closed position. The near-infra red light produced by the lighting subsystem transilluminates the tissue and is readily detected by laparoscopes or robotic laparoscopic camera. The light directly indicates where the instrument is positioned, which aids with visualizing the location of the inner lumen. Since the tissue scatters and absorbs the light, transilluminating through a thinner tissue is observed as a brighter light pattern. The NIR emitters are spaced 25 mm apart, which can be used as a length reference.

If during the procedure, the surgeon needs to modify the gastric anatomy by removing portion of the stomach, the placing of the instrument's sizing tube inside of the stomach provides information about position of the gastric lumen. While unrelated to the transilluminating light functionality, it is noteworthy that in its capacity as a sizing guide, the sizing tube helps ensure that after the resection, the remaining gastric anatomy maintains the desired patency.

The established approach to visualizing the instrument while inside of GI tract involves surgeon manipulating the tissue around the device with graspers and/or applying suction to decompress the stomach to make the stomach wall adhere to the tube, forming a clear delineation line that visualizes where the tube is located.

The added light emitting functionality of the instrument 520, or any other embodiment of an instrument including an illuminated sizing tube constructed in accordance with this invention further aids visualization by the means of the NIR transillumination. The NIR wavelength is suited to pass through several mm of stomach (or other) tissue. Light emitted from the NIR diodes is scattered through the wall of the tube and then further scattered as it transilluminates tissue. When observed from the outside of the stomach, this transillumination forms a diffuse light pattern that clearly locates the device within the stomach. The NIR based visualization is clear, without the need to manipulate the tissue with graspers or to decompress it by applying suction.

While the above discussion of the instrument 520 has been primarily focused on use in the stomach, e.g., for a sleeve gastrectomy and for gastric bypass, the instrument has other uses as well. In particular, the added light functionality is very likely to be helpful to the surgeon in other procedures. A few examples of those procedures are as follows. Surgeons may advance the distal end of the sizing tube into communicating anatomical structures, e.g., as far as the pyloric valve. Similarly, they may be working in other anatomical communicating structures, e.g., around the gastro-esophageal junction, such as but not limited to fundoplications, hiatal hernia repairs, gastric anastomoses, or higher on the esophagus, such as but not limited to foregut surgery, or even during thoracic surgery.

As should be appreciated by those skilled in the art, the transilluminating light provided by the instrument 520 or any other instrument including an illuminated sizing tube may be of value in the pyloric valve or in the gastroesophageal junction or in the stomach itself, the transillumination pattern may (or may not) help the surgeon judge the thickness of the wall. This is because "thicker means less light, thinner means more light". It helps with "seeing the lumen" in GI tract in general. In some context, the light may help assure the surgeon about position of critical anatomic landmarks without them needing to "mobilize the anatomy"—meaning they don't have to "dig around and cauterize and separate" the anatomy to see "what is what". Thus, the light produced may help the surgeon or other user instantly see position and direction of the gastric/esophageal lumen and proceed with stomach resection without the need to mobilize tissue around the GE junction. This should save time.

In complex revisional surgeries (where the patient underwent more than one preceding procedure), extensive adhesions hamper identification of anatomy. The surgeon can spend up to 45 or more minutes taking down adhesions and mobilizing the stomach (or other anatomy) before they can safely proceed with the primary goal of the procedure. Having the lumen transilluminated in these cases is expected to be tremendously helpful.

In accordance with a preferred embodiment of the invention the NIR emitters are spaced 25 mm apart. This spacing can be seen quite clearly and it can serve as a length reference (although it should not be deemed to be a precise "measuring device"). Offering a length reference is helpful as often times as surgeons strive to keep certain geometry constant between the patients, to achieve good outcomes more consistently. For example, during the stapling of the resection line along the visually perceptible line produced by the application of suction to the wall of the stomach and with the additional visualization provided by the NIR light emitted, the first stapler fire is to be 6 cm from pyloric valve. Another example is the last stapler fire—which is supposed to leave approximately 1 cm of tissue from the gastroesophageal junction. In another example, the surgeon may desire to size the gastric pouch during gastric bypass. Moreover, surgeons often use clues from the surgical field of view for length reference (e.g., size of the graspers). Thus, the 25 mm spacing of the NIR lights is not the only feature in sight to help them with this. Nonetheless the NIR spacing can provide surgeons with additional length reference.

As should be appreciated by those skilled in the art from the foregoing description, the system 500, and any other system of this invention constructed like it, provides a non-sterile, single patient use device for use in gastric and bariatric surgery on a patient. It can be used to apply suction, decompress the stomach, drain gastric fluids, irrigate and serve as a sizing guide. That system is derived from the systems of the application of the assignee as identified above with the addition of battery powered LED lights, To that end, the instrument of the subject system comprises a sizing tube having a circular outer surface and terminating at a closed, rounded atraumatic tip. The sizing tube includes an array of plural apertures extending about the circular outer surface of a distal portion of the sizing tube adjacent the atraumatic tip. The proximal end portion of the instrument includes a slide valve, an integral suction regulator and a battery housing including a battery case. The battery case includes two AAA non-rechargeable alkaline batteries to power an illumination source located within the central passageway in the distal end portion of the sizing tube. That illumination source comprises a flexible circuit including a visible red LED and plural spaced apart near infrared LEDs. The LEDs emit light that is readily detected by NIR-sensitive laparoscopes. The purpose of the LED lights is to aid visualization of the sizing tube by tissue transillumination during insertion of the sizing tube and surgery under laparoscopic vision. The instrument's sizing tube is inserted into the patient via the patient's esophagus by an anesthesiologist, typically under supervision of a surgeon. The LEDs of the illumination source do not change the intended use of the instrument and are not required for the surgery to proceed safely, but they do provide an added measure of visualization to aid in the surgery.

It must be pointed out at this juncture that the various components of the instruments shown and described above are merely exemplary of various components that may be used in accordance with this invention to provide the capabilities as discussed above.

Without further elaboration the foregoing will so fully illustrate our invention that others may, by applying current or future knowledge, adopt the same for use under various conditions of service.

We claim:

1. An instrument for a bariatric procedure on a patient having a stomach, the stomach having a wall, a greater curvature and a lesser curvature, the patient also having an esophagus, said instrument comprising:

a sizing tube formed as an elongated unitary member of a flexible non-expandable material having a predetermined outside diameter configured for introduction through the esophagus into the patient's stomach so that a portion of said sizing tube is disposed along the lesser curvature of the patient's stomach, said sizing tube having a longitudinal axis and a circular cross-section having a circular outer surface, whereupon when said sizing tube is disposed along the lesser curvature of the patient's stomach the entire circular outer surface of said sizing tube is exposed for engagement by portions of the patient's stomach, said sizing tube having a distal end portion, a proximal end portion, a hollow interior defining a passageway, and a plurality of apertures disposed about said circular outer surface at said distal end portion, said plurality of apertures being directed in a plurality of different radial directions extending at an angle greater than zero degrees from each other measured about said longitudinal axis and being in fluid communication with said passageway, plural ones of said apertures extending along a first portion of said longitudinal axis and along a portion of the lesser curvature of the patient's stomach when said sizing tube is located within the patient's stomach, said sizing tube including an elongated electronic source of illumination extending along said first portion of said longitudinal axis and electrical conductors coupled to said elongated electronic source of illumination, said elongated electronic source of illumination and said electrical conductors being encased and sealed within a flexible sleeve located within said sizing tube, said electrical conductors being configured for coupling to an electrical power source for causing said electronic source of illumination to produce near infra-red light when electrical energy is applied to said electrical conductors from said electrical power source, said instrument being configured for providing controlled suction to said passageway and through said apertures to pull the lesser curvature of the patient's stomach into engagement with a portion of said circular outer surface of said sizing tube and contemporaneously therewith to pull other portions of the patient's stomach adjacent to said sizing tube towards portions of said circular outer surface of said sizing tube not facing the lesser curvature of the patient's stomach to produce a suction-created visually perceptible delineation line on the exterior of the patient's stomach along a portion of said circular outer surface of said sizing tube facing the greater curvature of the patient's stomach, said electronic source of illumination being configured for producing near infrared light into the patient's stomach when energized by an electrical power source via said electrical conductors, whereupon the position of said sizing tube within the patient's stomach can be readily visualized laparoscopically from outside the wall of patient's stomach by transillumination of the near infrared light passing through the wall of the patient's stomach.

2. The instrument of claim 1 additionally comprising an electronic source of visible light coupled to said elongated electronic source of illumination, said electronic source of visible light being configured to produce visible light indicating operation of the elongated electronic source of illumination producing said near infrared light.

3. The instrument of claim 1 wherein said near infrared light is in the range of 780 nm to 880 nm.

4. The instrument of claim 3 wherein said near infrared light is preferably 850 nanometers.

5. The instrument of claim 1 wherein said elongated electronic source of illumination comprises a flexible circuit including plural spaced-apart near infrared light emitting diodes.

6. The instrument of claim 1 wherein said electronic source of visible light comprises at least one light emitting diode for producing said visible light.

7. The instrument of claim 1 wherein the electrical power source is an electrical battery, wherein said instrument comprises said electrical battery, and wherein said electrical battery is connected to said source of illumination.

8. The instrument of claim 1 wherein said sizing tube is configured to permit flexing of said sizing tube perpendicular to said longitudinal axis while preventing longitudinal collapse thereof due to perpendicular flexion.

9. The instrument of claim 8 additionally comprising a spring located in said distal end portion of said sizing tube, said spring being configured to permit flexing of said sizing tube perpendicular to said longitudinal axis while preventing longitudinal collapse of said sizing tube due to perpendicular flexion.

10. The instrument of claim 1 wherein said sizing tube includes at least one one-way valve, said at least one one-way valve being automatically closed when controlled suction is applied to said passageway, said at least one one-way valve being openable to enable a fluid to be passed therethrough from the interior of said sizing tube into the stomach of the patient to prevent said sizing tube from becoming stuck in the patient's stomach.

11. The instrument of claim 10 wherein said at least one one-way valve comprises a slit in said sidewall.

12. The instrument of claim 1 wherein said instrument comprises a portion of a system, said system additionally comprising a suction controller configured to apply controlled suction from a source of suction to said passageway of said sizing tube to result in a force in a range of 0.05 to 200 pounds anchoring said sizing tube in position within the patient's stomach.

13. The instrument of claim 1, wherein said sizing tube is configured to apply a suction force per unit length within the patient's stomach at the location of said apertures when said controlled suction is applied to said passageway, whereupon the suction force applied per unit length is in a range of 0.02 to 21 pounds per inch.

14. An instrument for a bariatric procedure on a patient having a stomach, the stomach having a wall, a greater curvature and a lesser curvature, the patient also having an esophagus, said instrument comprising:

a sizing tube formed as an elongated unitary member of a flexible non-expandable material having a predetermined outside diameter configured for introduction through the esophagus into the patient's stomach so that a portion of said sizing tube is disposed along the lesser curvature of the patient's stomach, said sizing tube having a longitudinal axis and a circular cross-section having a circular outer surface, whereupon when said sizing tube is disposed along the lesser curvature of the patient's stomach the entire circular outer surface of said sizing tube is exposed for engagement by portions of the patient's stomach, said sizing tube having a distal end portion, a proximal end portion, a hollow interior defining a passageway, and a plurality of apertures disposed about said circular outer surface at said distal end portion, said plurality of apertures being directed in a plurality of different radial directions extending at an angle greater than zero degrees from each other measured about said longitudinal axis and being in fluid communication with said passageway, plural ones of said apertures extending along a first portion of said longitudinal axis and along a portion of the lesser curvature of the patient's stomach when said sizing tube is located within the patient's stomach, said sizing tube including an elongated electronic source of illumination extending along said first portion of said longitudinal axis and electrical conductors coupled to said elongated electronic source of illumination, said electrical conductors being configured for connection to an electrical power source for causing said electronic source of illumination to produce near infra-red light when electrical energy is applied to said electrical conductors from said electrical power source, said instrument being configured for providing controlled suction to said passageway and through said apertures to pull the lesser curvature of the patient's stomach into engagement with a portion of said circular outer surface of said sizing tube and contemporaneously therewith to pull other portions of the patient's stomach adjacent to said sizing tube towards portions of said circular outer surface of said sizing tube not facing the lesser curvature of the patient's stomach to produce a suction-created visually perceptible delineation line on the exterior of the patient's stomach along a portion of said circular outer surface of said sizing tube facing the greater curvature of the patient's stomach, said electronic source of illumination being configured for producing near infra-red light into the patient's stomach when energized by an electrical power source via said electrical conductors, whereupon the position of said sizing tube within the patient's stomach can be readily visualized laparoscopically from outside the wall of patient's stomach by transillumination of the near infrared light passing through the wall of the patient's stomach, said instrument additionally comprising an electronic source of visible light coupled to said elongated electronic source of illumination, said electronic source of visible light being configured to produce visible light indicating operation of the elongated electronic source of illumination producing said near infrared light.

15. The instrument of claim 14 wherein said near infrared light is in the range of 780 nm to 880 nm.

16. The instrument of claim 15 wherein said near infrared light is preferably 850 nanometers.

17. The instrument of claim 14 wherein said electronic source of visible light comprises at least one light emitting diode for producing said visible light.

18. The instrument of claim 17 wherein said least one light emitting diode for producing said visible light is located at said distal end portion.

19. The instrument of claim 14 wherein the electrical power source is an electrical battery, wherein said instrument comprises said electrical battery, and wherein said electrical battery is connected to said elongated electronic source of illumination and said electronic source of visible light.

* * * * *